US008697358B2

(12) United States Patent
Wirth et al.

(10) Patent No.: US 8,697,358 B2
(45) Date of Patent: Apr. 15, 2014

(54) NON-INVASIVE METHOD FOR DIAGNOSIS OF PROSTATE CANCER

(75) Inventors: Manfred Wirth, Dresden (DE); Susanne Fuessel, Dresden (DE); Rainer Koch, Radebeul (DE)

(73) Assignee: Technische Universitaet Dresden, Dresden (DE)

( * ) Notice: Subject to any disclaimer, the term of this patent is extended or adjusted under 35 U.S.C. 154(b) by 0 days.

(21) Appl. No.: 13/516,070

(22) PCT Filed: Dec. 15, 2010

(86) PCT No.: PCT/EP2010/069810

§ 371 (c)(1), (2), (4) Date: Aug. 28, 2012

(87) PCT Pub. No.: WO2011/073283

PCT Pub. Date: Jun. 23, 2011

(65) Prior Publication Data

US 2013/0035250 A1 Feb. 7, 2013

(30) Foreign Application Priority Data

Dec. 15, 2009 (EP) .................................... 09179327

(51) Int. Cl.
*C12Q 1/68* (2006.01)
*C40B 30/04* (2006.01)

(52) U.S. Cl.
USPC ................................ 435/6.1; 435/6.12; 506/9

(58) Field of Classification Search
None
See application file for complete search history.

(56) References Cited

U.S. PATENT DOCUMENTS

2003/0077618 A1 4/2003 O'Brien et al.
2006/0211017 A1* 9/2006 Chinnaiyan et al. .............. 435/6

FOREIGN PATENT DOCUMENTS

WO WO 01/62271 8/2001
WO WO 03/012067 2/2003
WO WO 2006/056766 6/2006

OTHER PUBLICATIONS

Schmidt et al. Quantitative Multi-Gene Expression Profiling of Primary Prostate Cancer. 2006. The Prostate. vol. 66, pp. 1521-1534.*
Laxman, Bharathi, et al.: "A First Generation Multiplex Biomarker Analysis of Urine for the Early Detection of Prostate Cancer," Cancer Research, vol. 68(3), pp. 645-619, 2008.
Schneider, S. et al.: "Molecular Genetic Markers for Prostate Cancer. Evidence in Fine Needle Biopsies for Improved Confirmation of the Diagnosis," Der Urologe, Ausg. A, vol. 47(9), pp. 1208-1211, 2008.
Vasileva, E., et al.: "Detection of GSTP1 Hypermethylation and Hepsin Activity for Prostate Non-Invasive Cancer Diagnostics," Journal of Urology, vol. 179(4), p. 685, Abstract 1991, 2008.
International Search Report issued on Feb. 21, 2011 in International Application No. PCT/EP2010/069810.

* cited by examiner

*Primary Examiner* — Anne Gussow
*Assistant Examiner* — Channing S Mahatan
(74) *Attorney, Agent, or Firm* — Fanelli Hang & Kilger PLLC

(57) ABSTRACT

The present invention relates on a non-invasive method for diagnosing prostate cancer and/or assessing the risk of a subject acquiring prostate cancer comprising the analysis of the expression of the marker gene hepsin in an urine sample. It further relates on a non-invasive method for diagnosing prostate cancer and/or assessing the risk of a subject acquiring prostate cancer by determining the expression levels of the marker genes hepsin, EZH2, prostein and PCA3.

5 Claims, 2 Drawing Sheets

SEQUENCE LISTING

<160> NUMBER OF SEQ ID NOS: 38

<210> SEQ ID NO 1
<211> LENGTH: 1809
<212> TYPE: DNA
<213> ORGANISM: Homo sapiens
<300> PUBLICATION INFORMATION:
<308> DATABASE ACCESSION NUMBER: GenBank/NM_002151
<309> DATABASE ENTRY DATE: 2009-04-23
<313> RELEVANT RESIDUES IN SEQ ID NO: (1)..(1809)

<400> SEQUENCE: 1

```
tcgagcccgc tttccaggga ccctacctga gggcccacag gtgaggcagc ctggcctagc     60

aggccccacg ccaccgcctc tgcctccagg ccgcccgctg ctgcggggcc accatgctcc    120

tgcccaggcc tggagactga cccgaccccg gcactacctc gaggctccgc ccccacctgc    180

tggaccccag ggtcccaccc tggcccagga ggtcagccag ggaatcatta acaagaggca    240

gtgacatggc gcagaaggag ggtggccgga ctgtgccatg ctgctccaga cccaaggtgg    300

cagctctcac tgcggggacc ctgctacttc tgacagccat cggggcggca tcctgggcca    360

ttgtggctgt tctcctcagg agtgaccagg agccgctgta cccagtgcag gtcagctctg    420

cggacgctcg gctcatggtc tttgacaaga cggaagggac gtggcggctg ctgtgctcct    480

cgcgctccaa cgccagggta gccggactca gctgcgagga gatgggcttc ctcagggcac    540

tgacccactc cgagctggac gtgcgaacgg cgggcgccaa tggcacgtcg ggcttcttct    600

gtgtggacga ggggaggctg ccccacaccc agaggctgct ggaggtcatc tccgtgtgtg    660

attgccccag aggccgtttc ttggccgcca tctgccaaga ctgtggccgc aggaagctgc    720

ccgtggaccg catcgtggga ggccgggaca ccagcttggg ccggtggccg tggcaagtca    780

gccttcgcta tgatggagca cacctctgtg gggatccct gctctccggg gactgggtgc     840

tgacagccgc ccactgcttc ccggagcgga accgggtcct gtcccgatgg cgagtgtttg    900

ccggtgccgt ggcccaggcc tctccccacg gtctgcagct gggggtgcag gctgtggtct    960

accacggggg ctatcttccc tttcgggacc ccaacagcga ggagaacagc aacgatattg   1020
```

-continued

```
ccctggtcca cctctccagt cccctgcccc tcacagaata catccagcct gtgtgcctcc   1080

cagctgccgg ccaggccctg gtggatggca agatctgtac cgtgacgggc tggggcaaca   1140

cgcagtacta tggccaacag gccggggtac tccaggaggc tcgagtcccc ataatcagca   1200

atgatgtctg caatggcgct gacttctatg gaaaccagat caagcccaag atgttctgtg   1260

ctggctaccc cgagggtggc attgatgcct gccagggcga cagcggtggt ccctttgtgt   1320

gtgaggacag catctctcgg acgccacgtt ggcggctgtg tggcattgtg agttggggca   1380

ctggctgtgc cctggcccag aagccaggcg tctacaccaa agtcagtgac ttccgggagt   1440

ggatcttcca ggccataaag actcactccg aagccagcgg catggtgacc cagctctgac   1500

cggtggcttc tcgctgcgca gcctccaggg cccgaggtga tcccggtggt gggatccacg   1560

ctgggcctag gatgggacgt tttttcttct gggcccggtc cacaggtcca aggacaccct   1620

ccctccaggg tcctctcttc cacagtggcg ggcccactca gccccgagac cacccaacct   1680

caccctcctg acccccatgt aaatattgtt ctgctgtctg ggactcctgt ctaggtgccc   1740

ctgatgacgg gatgctcttt aaataataaa gatggttttg attaaaaaaa aaaaaaaaaa   1800

aaaaaaaaa                                                           1809
```

<210> SEQ ID NO 2
<211> LENGTH: 1867
<212> TYPE: DNA
<213> ORGANISM: Homo sapiens
<300> PUBLICATION INFORMATION:
<308> DATABASE ACCESSION NUMBER: GenBank/NM_003194
<309> DATABASE ENTRY DATE: 2009-12-06
<313> RELEVANT RESIDUES IN SEQ ID NO: (1)..(1867)

<400> SEQUENCE: 2

```
ggttcgctgt ggcgggcgcc tgggccgccg gctgtttaac ttcgcttccg ctggcccata     60

gtgatctttg cagtgaccca gcagcatcac tgtttcttgg cgtgtgaaga taacccaagg    120

aattgaggaa gttgctgaga agagtgtgct ggagatgctc taggaaaaaa ttgaatagtg    180

agacgagttc cagcgcaagg gtttctggtt tgccaagaag aaagtgaaca tcatggatca    240

gaacaacagc ctgccacctt acgctcaggg cttggcctcc cctcagggtg ccatgactcc    300

cggaatccct atctttagtc caatgatgcc ttatggcact ggactgaccc cacagcctat    360

tcagaacacc aatagtctgt ctattttgga agagcaacaa aggcagcagc agcaacaaca    420

acagcagcag cagcagcagc agcagcaaca gcaacagcag cagcagcagc agcagcagca    480

gcagcagcag cagcagcagc agcagcagca gcaacaggca gtggcagctg cagccgttca    540

gcagtcaacg tcccagcagg caacacaggg aacctcaggc caggcaccac agctcttcca    600

ctcacagact ctcacaactg caccccttgcc gggcaccact ccactgtatc cctcccccat    660

gactcccatg acccccatca ctcctgccac gccagcttcg gagagttctg ggattgtacc    720

gcagctgcaa aatattgtat ccacagtgaa tcttggttgt aaacttgacc taaagaccat    780

tgcacttcgt gcccgaaacg ccgaatataa tcccaagcgg tttgctgcgg taatcatgag    840

gataagagag ccacgaacca cggcactgat tttcagttct gggaaaatgg tgtgcacagg    900

agccaagagt gaagaacagt ccagactggc agcaagaaaa tatgctagag ttgtacagaa    960

gttgggtttt ccagctaagt tcttggactt caagattcag aatatggtgg ggagctgtga   1020

tgtgaagttt cctataaggt tagaaggcct tgtgctcacc caccaacaat ttagtagtta   1080

tgagccagag ttatttcctg gtttaatcta cagaatgatc aaacccagaa ttgttctcct   1140

tatttttgtt tctggaaaag ttgtattaac aggtgctaaa gtcagagcag aaatttatga   1200
```

```
agcatttgaa aacatctacc ctattctaaa gggattcagg aagacgacgt aatggctctc   1260

atgtaccctt gcctccccca ccccccttctt tttttttttt taaacaaatc agtttgtttt   1320

ggtaccttta aatggtggtg ttgtgagaag atggatgttg agttgcaggg tgtggcacca   1380

ggtgatgccc ttctgtaagt gcccaccgcg ggatgccggg aaggggcatt atttgtgcac   1440

tgagaacacc gcgcagcgtg actgtgagtt gctcataccg tgctgctatc tgggcagcgc   1500

tgcccattta tttatatgta gattttaaac actgctgttg acaagttggt ttgagggaga   1560

aaactttaag tgttaaagcc acctctataa ttgattggac tttttaattt taatgttttt   1620

ccccatgaac cacagttttt atatttctac cagaaaagta aaaatctttt ttaaaagtgt   1680

tgtttttcta atttataact cctaggggtt atttctgtgc cagacacatt ccacctctcc   1740

agtattgcag gacagaatat atgtgttaat gaaaatgaat ggctgtacat atttttttct   1800

ttcttcagag tactctgtac aataaatgca gtttataaaa gtgttaaaaa aaaaaaaaaa   1860

aaaaaaa                                                              1867
```

<210> SEQ ID NO 3
<211> LENGTH: 1464
<212> TYPE: DNA
<213> ORGANISM: Homo sapiens
<300> PUBLICATION INFORMATION:
<308> DATABASE ACCESSION NUMBER: GenBank/NM_001648
<309> DATABASE ENTRY DATE: 2009-12-06
<313> RELEVANT RESIDUES IN SEQ ID NO: (1)..(1464)

<400> SEQUENCE: 3

```
agccccaagc ttaccacctg cacccggaga gctgtgtcac catgtgggtc ccggttgtct     60

tcctcaccct gtccgtgacg tggattggtg ctgcacccct catcctgtct cggattgtgg    120

gaggctggga gtgcgagaag cattcccaac cctggcaggt gcttgtggcc tctcgtggca    180

gggcagtctg cggcggtgtt ctggtgcacc cccagtgggt cctcacagct gcccactgca    240

tcaggaacaa aagcgtgatc ttgctgggtc ggcacagcct gtttcatcct gaagacacag    300

gccaggtatt tcaggtcagc cacagcttcc cacacccgct ctacgatatg agcctcctga    360

agaatcgatt cctcaggcca ggtgatgact ccagccacga cctcatgctg ctccgcctgt    420

cagagcctgc cgagctcacg gatgctgtga aggtcatgga cctgcccacc caggagccag    480

cactggggac cacctgctac gcctcaggct ggggcagcat tgaaccagag gagttcttga    540

ccccaaagaa acttcagtgt gtggacctcc atgttatttc caatgacgtg tgtgcgcaag    600

ttcaccctca gaaggtgacc aagttcatgc tgtgtgctgg acgctggaca gggggcaaaa    660

gcacctgctc gggtgattct gggggcccac ttgtctgtaa tggtgtgctt caaggtatca    720

cgtcatgggg cagtgaacca tgtgccctgc ccgaaaggcc ttccctgtac accaaggtgg    780

tgcattaccg gaagtggatc aaggacacca tcgtggccaa cccctgagca cccctatcaa    840

ccccctattg tagtaaactt ggaaccttgg aaatgaccag gccaagactc aagcctcccc    900

agttctactg acctttgtcc ttaggtgtga ggtccagggt tgctaggaaa agaaatcagc    960

agacacaggt gtagaccaga gtgtttctta aatggtgtaa ttttgtcctc tctgtgtcct   1020

ggggaatact ggccatgcct ggagacatat cactcaattt ctctgaggac acagatagga   1080

tggggtgtct gtgttatttg tggggtacag agatgaaaga ggggtgggat ccacactgag   1140

agagtggaga gtgacatgtg ctggacactg tccatgaagc actgagcaga agctggaggc   1200

acaacgcacc agacactcac agcaaggatg gagctgaaaa cataacccac tctgtcctgg   1260

aggcactggg aagcctagag aaggctgtga gccaaggagg gagggtcttc ctttggcatg   1320
```

```
ggatggggat gaagtaagga gagggactgg accccctgga agctgattca ctatgggggg   1380

aggtgtattg aagtcctcca gacaaccctc agatttgatg atttcctagt agaactcaca   1440

gaaataaaga gctgttatac tgtg                                          1464


<210> SEQ ID NO 4
<211> LENGTH: 3735
<212> TYPE: DNA
<213> ORGANISM: Homo sapiens
<300> PUBLICATION INFORMATION:
<308> DATABASE ACCESSION NUMBER: GenBank/NR_015342
<309> DATABASE ENTRY DATE: 2009-10-11
<313> RELEVANT RESIDUES IN SEQ ID NO: (1)..(3735)

<400> SEQUENCE: 4

agaagaaata gcaagtgccg agaagctggc atcagaaaaa cagaggggag atttgtgtgg     60

ctgcagccga gggagaccag gaagatctgc atggtgggaa ggacctgatg atacagaggt    120

gagaaataag aaaggctgct gactttacca tctgaggcca cacatctgct gaaatggaga    180

taattaacat cactagaaac agcaagatga caatataatg tctaagtagt gacatgtttt    240

tgcacatttc cagccccttt aaatatccac acacacagga agcacaaaag gaagcacaga    300

gatccctggg agaaatgccc ggccgccatc ttgggtcatc gatgagcctc gccctgtgcc    360

tggtcccgct tgtgagggaa ggacattaga aaatgaattg atgtgttcct taaaggatgg    420

gcaggaaaac agatcctgtt gtggatattt atttgaacgg gattacagat ttgaaatgaa    480

gtcacaaagt gagcattacc aatgagagga aaacagacga gaaaatcttg atggcttcac    540

aagacatgca acaaacaaaa tggaatactg tgatgacatg aggcagccaa gctggggagg    600

agataaccac ggggcagagg gtcaggattc tggccctgct gcctaaactg tgcgttcata    660

accaaatcat ttcatatttc taaccctcaa aacaaagctg ttgtaatatc tgatctctac    720

ggttccttct gggcccaaca ttctccatat atccagccac actcattttt aatatttagt    780

tcccagatct gtactgtgac ctttctacac tgtagaataa cattactcat tttgttcaaa    840

gacccttcgt gttgctgcct aatatgtagc tgactgtttt tcctaaggag tgttctggcc    900

caggggatct gtgaacaggc tgggaagcat ctcaagatct ttccagggtt atacttacta    960

gcacacagca tgatcattac ggagtgaatt atctaatcaa catcatcctc agtgtctttg   1020

cccatactga aattcatttc ccacttttgt gcccattctc aagacctcaa aatgtcattc   1080

cattaatatc acaggattaa cttttttttt taacctggaa gaattcaatg ttacatgcag   1140

ctatgggaat ttaattacat attttgtttt ccagtgcaaa gatgactaag tcctttatcc   1200

ctcccctttg tttgattttt tttccagtat aaagttaaaa tgcttagcct tgtactgagg   1260

ctgtatacag ccacagcctc tccccatccc tccagcctta tctgtcatca ccatcaaccc   1320

ctcccatgca cctaaacaaa atctaacttg taattccttg aacatgtcag gcatacatta   1380

ttccttctgc ctgagaagct cttccttgtc tcttaaatct agaatgatgt aaagttttga   1440

ataagttgac tatcttactt catgcaaaga agggacacat atgagattca tcatcacatg   1500

agacagcaaa tactaaaagt gtaatttgat tataagagtt tagataaata tatgaaatgc   1560

aagagccaca gagggaatgt ttatggggca cgtttgtaag cctgggatgt gaagcaaagg   1620

cagggaacct catagtatct tatataatat acttcatttc tctatctcta tcacaatatc   1680

caacaagctt ttcacagaat tcatgcagtg caaatcccca aaggtaacct ttatccattt   1740

catggtgagt gcgctttaga attttggcaa atcatactgg tcacttatct caactttgag   1800

atgtgtttgt ccttgtagtt aattgaaaga aatagggcac tcttgtgagc cactttaggg   1860
```

```
ttcactcctg gcaataaaga atttacaaag agctactcag gaccagttgt taagagctct   1920

gtgtgtgtgt gtgtgtgtgt gagtgtacat gccaaagtgt gcctctctct ctttgaccca   1980

ttatttcaga cttaaaaaca agcatgtttt caaatggcac tatgagctgc caatgatgta   2040

tcaccaccat atctcattat tctccagtaa atgtgataat aatgtcatct gttaacataa   2100

aaaaagtttg acttcacaaa agcagctgga aatggacaac cacaatatgc ataaatctaa   2160

ctcctaccat cagctacaca ctgcttgaca tatattgtta gaagcacctc gcatttgtgg   2220

gttctcttaa gcaaaatact tgcattaggt ctcagctggg gctgtgcatc aggcggtttg   2280

agaaatattc aattctcagc agaagccaga atttgaattc cctcatcttt taggaatcat   2340

ttaccaggtt tggagaggat tcagacagct caggtgcttt cactaatgtc tctgaacttc   2400

tgtccctctt tgtgttcatg gatagtccaa taaataatgt tatctttgaa ctgatgctca   2460

taggagagaa tataagaact ctgagtgata tcaacattag ggattcaaag aaatattaga   2520

tttaagctca cactggtcaa aaggaaccaa gatacaaaga actctgagct gtcatcgtcc   2580

ccatctctgt gagccacaac caacagcagg acccaacgca tgtctgagat ccttaaatca   2640

aggaaaccag tgtcatgagt tgaattctcc tattatggat gctagcttct ggccatctct   2700

ggctctcctc ttgacacata ttagcttcta gcctttgctt ccacgacttt tatcttttct   2760

ccaacacatc gcttaccaat cctctctctg ctctgttgct ttggacttcc ccacaagaat   2820

ttcaacgact ctcaagtctt ttcttccatc cccaccacta acctgaatgc ctagaccctt   2880

atttttatta atttccaata gatgctgcct atgggctata ttgctttaga tgaacattag   2940

atatttaaag ctcaagaggt tcaaaatcca actcattatc ttctctttct ttcacctccc   3000

tgctcctctc cctatattac tgattgcact gaacagcatg gtccccaatg tagccatgca   3060

aatgagaaac ccagtggctc cttgtggtac atgcatgcaa gactgctgaa gccagaagga   3120

tgactgatta cgcctcatgg gtggagggga ccactcctgg gccttcgtga ttgtcaggag   3180

caagacctga gatgctccct gccttcagtg tcctctgcat ctcccctttc taatgaagat   3240

ccatagaatt tgctacattt gagaattcca attaggaact cacatgtttt atctgcccta   3300

tcaatttttt aaacttgctg aaaattaagt tttttcaaaa tctgtccttg taaattactt   3360

tttcttacag tgtcttggca tactatatca actttgattc tttgttacaa cttttcttac   3420

tcttttatca ccaaagtggc ttttattctc tttattatta ttattttctt ttactactat   3480

attacgttgt tattattttg ttctctatag tatcaattta tttgatttag tttcaattta   3540

tttttattgc tgacttttaa aataagtgat tcggggggtg ggagaacagg ggagggagag   3600

cattaggaca aatacctaat gcatgtggga cttaaaacct agatgatggg ttgataggtg   3660

cagcaaacca ctatggcaca cgtatacctg tgtaacaaac ctacacattc tgcacatgta   3720

tcccagaacg taaag                                                    3735
```

```
<210> SEQ ID NO 5
<211> LENGTH: 3923
<212> TYPE: DNA
<213> ORGANISM: Homo sapiens
<300> PUBLICATION INFORMATION:
<308> DATABASE ACCESSION NUMBER: GenBank/AF103907
<309> DATABASE ENTRY DATE: 2000-08-14
<313> RELEVANT RESIDUES IN SEQ ID NO: (1)..(3923)

<400> SEQUENCE: 5

acagaagaaa tagcaagtgc cgagaagctg gcatcagaaa aacagagggg agatttgtgt     60

ggctgcagcc gagggagacc aggaagatct gcatggtggg aaggacctga tgatacagag    120
```

```
gaattacaac acatatactt agtgtttcaa tgaacaccaa gataaataag tgaagagcta    180
gtccgctgtg agtctcctca gtgacacagg gctggatcac catcgacggc actttctgag    240
tactcagtgc agcaaagaaa gactacagac atctcaatgg caggggtgag aaataagaaa    300
ggctgctgac tttaccatct gaggccacac atctgctgaa atggagataa ttaacatcac    360
tagaaacagc aagatgacaa tataatgtct aagtagtgac atgtttttgc acatttccag    420
cccctttaaa tatccacaca cacaggaagc acaaaaggaa gcacagagat ccctgggaga    480
aatgcccggc cgccatcttg ggtcatcgat gagcctcgcc ctgtgcctgg tcccgcttgt    540
gagggaagga cattagaaaa tgaattgatg tgttccttaa aggatgggca ggaaaacaga    600
tcctgttgtg gatatttatt tgaacgggat tacagatttg aaatgaagtc acaaagtgag    660
cattaccaat gagaggaaaa cagacgagaa aatcttgatg gcttcacaag acatgcaaca    720
aacaaaatgg aatactgtga tgacatgagg cagccaagct ggggaggaga taaccacggg    780
gcagagggtc aggattctgg ccctgctgcc taaactgtgc gttcataacc aaatcatttc    840
atatttctaa ccctcaaaac aaagctgttg taatatctga tctctacggt tccttctggg    900
cccaacattc tccatatatc cagccacact catttttaat atttagttcc cagatctgta    960
ctgtgacctt tctacactgt agaataacat tactcatttt gttcaaagac ccttcgtgtt   1020
gctgcctaat atgtagctga ctgtttttcc taaggagtgt tctggcccag gggatctgtg   1080
aacaggctgg gaagcatctc aagatctttc cagggttata cttactagca cacagcatga   1140
tcattacgga gtgaattatc taatcaacat catcctcagt gtctttgccc atactgaaat   1200
tcatttccca cttttgtgcc cattctcaag acctcaaaat gtcattccat taatatcaca   1260
ggattaactt tttttttaa cctggaagaa ttcaatgtta catgcagcta tgggaattta   1320
attacatatt ttgttttcca gtgcaaagat gactaagtcc tttatccctc ccctttgttt   1380
gatttttttt ccagtataaa gttaaaatgc ttagccttgt actgaggctg tatacagcac   1440
agcctctccc catccctcca gccttatctg tcatcaccat caacccctcc cataccacct   1500
aaacaaaatc taacttgtaa ttccttgaac atgtcaggac atacattatt ccttctgcct   1560
gagaagctct tccttgtctc ttaaatctag aatgatgtaa agttttgaat aagttgacta   1620
tcttacttca tgcaaagaag ggacacatat gagattcatc atcacatgag acagcaaata   1680
ctaaaagtgt aatttgatta taagagttta gataaatata tgaaatgcaa gagccacaga   1740
gggaatgttt atggggcacg tttgtaagcc tgggatgtga agcaaaggca gggaacctca   1800
tagtatctta tataatatac ttcatttctc tatctctatc acaatatcca acaagctttt   1860
cacagaattc atgcagtgca aatccccaaa ggtaaccttt atccatttca tggtgagtgc   1920
gctttagaat tttggcaaat catactggtc acttatctca actttgagat gtgtttgtcc   1980
ttgtagttaa ttgaaagaaa tagggcactc ttgtgagcca ctttagggtt cactcctggc   2040
aataaagaat ttacaaagag ctactcagga ccagttgtta agagctctgt gtgtgtgtgt   2100
gtgtgtgtgt gagtgtacat gccaaagtgt gcctctctct cttgacccat tatttcagac   2160
ttaaaacaag catgttttca aatggcacta tgagctgcca atgatgtatc accaccatat   2220
ctcattattc tccagtaaat gtgataataa tgtcatctgt taacataaaa aaagtttgac   2280
ttcacaaaag cagctggaaa tggacaacca caatatgcat aaatctaact cctaccatca   2340
gctacacact gcttgacata tattgttaga agcacctcgc atttgtgggt tctcttaagc   2400
aaaatacttg cattaggtct cagctggggc tgtgcatcag gcggtttgag aaatattcaa   2460
ttctcagcag aagccagaat ttgaattccc tcatctttta ggaatcattt accaggtttg   2520
```

```
gagaggattc agacagctca ggtgctttca ctaatgtctc tgaacttctg tccctctttg   2580

tgttcatgga tagtccaata aataatgtta tctttgaact gatgctcata ggagagaata   2640

taagaactct gagtgatatc aacattaggg attcaaagaa atattagatt taagctcaca   2700

ctggtcaaaa ggaaccaaga tacaaagaac tctgagctgt catcgtcccc atctctgtga   2760

gccacaacca acagcaggac ccaacgcatg tctgagatcc ttaaatcaag gaaaccagtg   2820

tcatgagttg aattctccta ttatggatgc tagcttctgg ccatctctgg ctctcctctt   2880

gacacatatt agcttctagc ctttgcttcc acgactttta tcttttctcc aacacatcgc   2940

ttaccaatcc tctctctgct ctgttgcttt ggacttcccc acaagaattt caacgactct   3000

caagtctttt cttccatccc caccactaac ctgaatgcct agacccttat ttttattaat   3060

ttccaataga tgctgcctat gggctatatt gctttagatg aacattagat atttaaagct   3120

caagaggttc aaaatccaac tcattatctt ctctttcttt cacctccctg ctcctctccc   3180

tatattactg attgcactga acagcatggt ccccaatgta gccatgcaaa tgagaaaccc   3240

agtggctcct tgtggtacat gcatgcaaga ctgctgaagc cagaaggatg actgattacg   3300

cctcatgggt ggaggggacc actcctgggc cttcgtgatt gtcaggagca agacctgaga   3360

tgctccctgc cttcagtgtc ctctgcatct cccctttcta atgaagatcc atagaatttg   3420

ctacatttga gaattccaat taggaactca catgttttat ctgccctatc aatttttttaa   3480

acttgctgaa aattaagttt tttcaaaatc tgtccttgta aattactttt tcttacagtg   3540

tcttggcata ctatatcaac tttgattctt tgttacaact tttcttactc ttttatcacc   3600

aaagtggctt ttattctctt tattattatt attttctttt actactatat tacgttgtta   3660

ttattttgtt ctctatagta tcaatttatt tgatttagtt tcaatttatt tttattgctg   3720

acttttaaaa taagtgattc ggggggtggg agaacagggg agggagagca ttaggacaaa   3780

tacctaatgc atgtgggact taaaacctag atgatgggtt gataggtgca gcaaaccact   3840

atggcacacg tatacctgtg taacaaacct acacattctg cacatgtatc ccagaacgta   3900

aagtaaaatt taaaaaaaag tga                                            3923
```

```
<210> SEQ ID NO 6
<211> LENGTH: 2695
<212> TYPE: DNA
<213> ORGANISM: Homo sapiens
<300> PUBLICATION INFORMATION:
<308> DATABASE ACCESSION NUMBER: GenBank/NM_004456
<309> DATABASE ENTRY DATE: 2009-12-06
<313> RELEVANT RESIDUES IN SEQ ID NO: (1)..(2695)

<400> SEQUENCE: 6

caaataaaag cgatggcgat tgggctgccg cgtttggcgc tcggtccggt cgcgtccgac     60

acccggtggg actcagaagg cagtggagcc ccggcggcgg cggcggcggc gcgcgggggc    120

gacgcgcggg aacaacgcga gtcggcgcgc gggacgaaga ataatcatgg gccagactgg    180

gaagaaatct gagaagggac cagtttgttg gcggaagcgt gtaaaatcag agtacatgcg    240

actgagacag ctcaagaggt tcagacgagc tgatgaagta aagagtatgt ttagttccaa    300

tcgtcagaaa attttggaaa gaacggaaat cttaaaccaa gaatggaaac agcgaaggat    360

acagcctgtg cacatcctga cttctgtgag ctcattgcgc gggactaggg agtgttcggt    420

gaccagtgac ttggattttc caacacaagt catcccatta aagactctga atgcagttgc    480

ttcagtaccc ataatgtatt cttggtctcc cctacagcag aattttatgg tggaagatga    540

aactgtttta cataacattc cttatatggg agatgaagtt ttagatcagg atggtacttt    600
```

-continued

```
cattgaagaa ctaataaaaa attatgatgg gaaagtacac ggggatagag aatgtgggtt    660
tataaatgat gaaatttttg tggagttggt gaatgccctt ggtcaatata atgatgatga    720
cgatgatgat gatggagacg atcctgaaga aagagaagaa aagcagaaag atctggagga    780
tcaccgagat gataaagaaa gccgcccacc tcggaaattt ccttctgata aaatttttga    840
agccatttcc tcaatgtttc cagataaggg cacagcagaa gaactaaagg aaaaatataa    900
agaactcacc gaacagcagc tcccaggcgc acttcctcct gaatgtaccc ccaacataga    960
tggaccaaat gctaaatctg ttcagagaga gcaaagctta cactcctttc atacgctttt   1020
ctgtaggcga tgttttaaat atgactgctt cctacatcgt aagtgcaatt attcttttca   1080
tgcaacaccc aacacttata agcggaagaa cacagaaaca gctctagaca acaaaccttg   1140
tggaccacag tgttaccagc atttggaggg agcaaaggag tttgctgctg ctctcaccgc   1200
tgagcggata aagaccccac caaaacgtcc aggaggccgc agaagaggac ggcttcccaa   1260
taacagtagc aggcccagca cccccaccat taatgtgctg gaatcaaagg atacagacag   1320
tgatagggaa gcagggactg aaacgggggg agagaacaat gataaagaag aagaagagaa   1380
gaaagatgaa acttcgagct cctctgaagc aaattctcgg tgtcaaacac caataaagat   1440
gaagccaaat attgaacctc ctgagaatgt ggagtggagt ggtgctgaag cctcaatgtt   1500
tagagtcctc attggcactt actatgacaa tttctgtgcc attgctaggt taattgggac   1560
caaaacatgt agacaggtgt atgagtttag agtcaaagaa tctagcatca tagctccagc   1620
tcccgctgag gatgtggata ctcctccaag gaaaaagaag aggaaacacc ggttgtgggc   1680
tgcacactgc agaaagatac agctgaaaaa ggacggctcc tctaaccatg tttacaacta   1740
tcaaccctgt gatcatccac ggcagccttg tgacagttcg tgcccttgtg tgatagcaca   1800
aaatttttgt gaaaagtttt gtcaatgtag ttcagagtgt caaaaccgct ttccgggatg   1860
ccgctgcaaa gcacagtgca acaccaagca gtgcccgtgc tacctggctg tccgagagtg   1920
tgaccctgac ctctgtctta cttgtggagc cgctgaccat tgggacagta aaaatgtgtc   1980
ctgcaagaac tgcagtattc agcggggctc caaaaagcat ctattgctgg caccatctga   2040
cgtggcaggc tgggggattt ttatcaaaga tcctgtgcag aaaaatgaat tcatctcaga   2100
atactgtgga gagattattt ctcaagatga agctgacaga agagggaaag tgtatgataa   2160
atacatgtgc agctttctgt tcaacttgaa caatgatttt gtggtggatg caacccgcaa   2220
gggtaacaaa attcgttttg caaatcattc ggtaaatcca aactgctatg caaaagttat   2280
gatggttaac ggtgatcaca ggataggtat ttttgccaag agagccatcc agactggcga   2340
agagctgttt tttgattaca gatacagcca ggctgatgcc ctgaagtatg tcggcatcga   2400
aagagaaatg gaaatccctt gacatctgct acctcctccc ccctcctctg aaacagctgc   2460
cttagcttca ggaacctcga gtactgtggg caatttagaa aaagaacatg cagtttgaaa   2520
ttctgaattt gcaaagtact gtaagaataa tttatagtaa tgagtttaaa aatcaacttt   2580
ttattgcctt ctcaccagct gcaaagtgtt ttgtaccagt gaatttttgc aataatgcag   2640
tatggtacat ttttcaactt tgaataaaga atacttgaac ttgtcaaaaa aaaaa        2695
```

```
<210> SEQ ID NO 7
<211> LENGTH: 5621
<212> TYPE: DNA
<213> ORGANISM: Homo sapiens
<300> PUBLICATION INFORMATION:
<308> DATABASE ACCESSION NUMBER: GenBank/NM_024080
<309> DATABASE ENTRY DATE: 2009-12-06
<313> RELEVANT RESIDUES IN SEQ ID NO: (1)..(5621)
```

<400> SEQUENCE: 7

```
aagaaaatcc tgcttgacaa aaaccgtcac ttaggaaaag atgtcctttc gggcagccag     60
gctcagcatg aggaacagaa ggaatgacac tctggacagc acccggaccc tgtactccag    120
cgcgtctcgg agcacagact tgtcttacag tgaaagcgac ttggtgaatt ttattcaagc    180
aaattttaag aaacgagaat gtgtcttctt taccaaagat tccaaggcca cggagaatgt    240
gtgcaagtgt ggctatgccc agagccagca catggaaggc acccagatca accaaagtga    300
gaaatggaac tacaagaaac acaccaagga atttcctacc gacgcctttg gggatattca    360
gtttgagaca ctggggaaga aagggaagta tatacgtctg tcctgcgaca cggacgcgga    420
aatcctttac gagctgctga cccagcactg gcacctgaaa acacccaacc tggtcatttc    480
tgtgaccggg ggcgccaaga acttcgccct gaagccgcgc atgcgcaaga tcttcagccg    540
gctcatctac atcgcgcagt ccaaaggtgc ttggattctc acgggaggca cccattatgg    600
cctgatgaag tacatcgggg aggtggtgag agataacacc atcagcagga gttcagagga    660
gaatattgtg gccattggca tagcagcttg gggcatggtc tccaaccggg acaccctcat    720
caggaattgc gatgctgagg gctatttttt agcccagtac cttatggatg acttcacaag    780
agatccactg tatatcctgg acaacaacca cacacatttg ctgctcgtgg acaatggctg    840
tcatggacat cccactgtcg aagcaaagct ccggaatcag ctagagaagt atatctctga    900
gcgcactatt caagattcca actatggtgg caagatcccc attgtgtgtt ttgcccaagg    960
aggtggaaaa gagactttga aagccatcaa tacctccatc aaaaataaaa ttccttgtgt   1020
ggtggtggaa ggctcgggcc agatcgctga tgtgatcgct agcctggtgg aggtggagga   1080
tgccctgaca tcttctgccg tcaaggagaa gctggtgcgc tttttacccc gcacggtgtc   1140
ccggctgcct gaggaggaga ctgagagttg gatcaaatgg ctcaaagaaa ttctcgaatg   1200
ttctcaccta ttaacagtta ttaaaatgga agaagctggg gatgaaattg tgagcaatgc   1260
catctcctac gctctataca aagccttcag caccagtgag caagacaagg ataactggaa   1320
tgggcagctg aagcttctgc tggagtggaa ccagctggac ttagccaatg atgagatttt   1380
caccaatgac cgccgatggg agtctgctga ccttcaagaa gtcatgttta cggctctcat   1440
aaaggacaga cccaagtttg tccgcctctt tctggagaat ggcttgaacc tacggaagtt   1500
tctcacccat gatgtcctca ctgaactctt ctccaaccac ttcagcacgc ttgtgtaccg   1560
gaatctgcag atcgccaaga attcctataa tgatgccctc ctcacgtttg tctggaaact   1620
ggttgcgaac ttccgaagag gcttccggaa ggaagacaga aatggccggg acgagatgga   1680
catagaactc cacgacgtgt ctcctattac tcggcacccc ctgcaagctc tcttcatctg   1740
ggccattctt cagaataaga aggaactctc caaagtcatt tgggagcaga ccaggggctg   1800
cactctggca gccctgggag ccagcaagct tctgaagact ctggccaaag tgaagaacga   1860
catcaatgct gctggggagt ccgaggagct ggctaatgag tacgagaccc gggctgttga   1920
gctgttcact gagtgttaca gcagcgatga agacttggca gaacagctgc tggtctattc   1980
ctgtgaagct tggggtggaa gcaactgtct ggagctggcg gtggaggcca cagaccagca   2040
tttcatcgcc cagcctgggg tccagaattt tctttctaag caatggtatg gagagatttc   2100
ccgagacacc aagaactgga agattatcct gtgtctgttt attataccct tggtgggctg   2160
tggctttgta tcatttagga agaaacctgt cgacaagcac aagaagctgc tttggtacta   2220
tgtggcgttc ttcacctccc ccttcgtggt cttctcctgg aatgtggtct tctacatcgc   2280
cttcctcctg ctgtttgcct acgtgctgct catggatttc cattcggtgc cacaccccc    2340
```

```
cgagctggtc ctgtactcgc tggtctttgt cctcttctgt gatgaagtga gacagtggta   2400
cgtaaatggg gtgaattatt ttactgacct gtggaatgtg atggacacgc tggggctttt   2460
ttacttcata gcaggaattg tatttcggct ccactcttct aataaaagct ctttgtattc   2520
tggacgagtc attttctgtc tggactacat tattttcact ctaagattga tccacatttt   2580
tactgtaagc agaaacttag gacccaagat tataatgctg cagaggatgc tgatcgatgt   2640
gttcttcttc ctgttcctct ttgcggtgtg gatggtggcc tttggcgtgg ccaggcaagg   2700
gatccttagg cagaatgagc agcgctggag gtggatattc cgttcggtca tctacgagcc   2760
ctacctggcc atgttcggcc aggtgcccag tgacgtggat ggtaccacgt atgactttgc   2820
ccactgcacc ttcactggga atgagtccaa gccactgtgt gtggagctgg atgagcacaa   2880
cctgccccgg ttccccgagt ggatcaccat cccccctggtg tgcatctaca tgttatccac   2940
caacatcctg ctggtcaacc tgctggtcgc catgtttggc tacacggtgg gcaccgtcca   3000
ggagaacaat gaccaggtct ggaagttcca gaggtacttc ctggtgcagg agtactgcag   3060
ccgcctcaat atccccttcc ccttcatcgt cttcgcttac ttctacatgg tggtgaagaa   3120
gtgcttcaag tgttgctgca aggagaaaaa catggagtct tctgtctgct gtttcaaaaa   3180
tgaagacaat gagactctgg catgggaggg tgtcatgaag gaaaactacc ttgtcaagat   3240
caacacaaaa gccaacgaca cctcagagga aatgaggcat cgatttagac aactggatac   3300
aaagcttaat gatctcaagg gtcttctgaa agagattgct aataaaatca aataaaactg   3360
tatgaactct aatggagaaa aatctaatta tagcaagatc atattaagga atgctgatga   3420
acaattttgc tatcgactac taaatgagag attttcagac ccctgggtac atggtggatg   3480
attttaaatc accctagtgt gctgagacct tgagaataaa gtgtgtgatt ggtttcatac   3540
ttgaagacgg atataaagga agaatatttc ctttatgtgt ttctccagaa tggtgcctgt   3600
ttctctctgt gtctcaatgc ctgggactgg aggttgatag tttaagtgtg ttcttaccgc   3660
ctcctttttc ctttaatctt atttttgatg aacacatata taggagaaca tctatcctat   3720
gaataagaac ctggtcatgc tttactcctg tattgttatt ttgttcattt ccaattgatt   3780
ctctactttt ccctttttttg tattatgtga ctaattagtt ggcatattgt taaaagtctc   3840
tcaaattagg ccagattcta aacatgctg cagcaagagg accccgctct cttcaggaaa   3900
agtgttttca tttctcagga tgcttcttac ctgtcagagg aggtgacaag gcagtctctt   3960
gctctcttgg actcaccagg ctcctattga aggaaccacc cccattccta aatatgtgaa   4020
aagtcgccca aaatgcaacc ttgaaaggca ctactgactt tgttcttatt ggatactcct   4080
cttattattt ttccattaaa aataatagct ggctattata gaaaatttag accatacaga   4140
gatgtagaaa gaacataaat tgtccccatt accttaaggt aatcactgct aacaatttct   4200
ggatggtttt tcaagtctat tttttttcta tgtatgtctc aattctcttt caaaatttta   4260
cagaatgtta tcatactaca tatatacttt ttatgtaagc tttttcactt agtattttat   4320
caaatatgtt tttattatat tcatagcctt cttaaacatt atatcaataa ttgcataata   4380
ggcaacctct agcgattacc ataattttgc tcattgaagg ctatctccag ttgatcattg   4440
ggatgagcat ctttgtgcat gaatcctatt gctgtatttg ggaaaatttt ccaaggttag   4500
attccaataa atatctattt attattaaat attaaaatat ctatttatta ttaaaaccat   4560
ttataaggct ttttcataaa tgtatagcaa ataggaatta ttaacttgag cataagatat   4620
gagatacatg aacctgaact attaaaataa aatattatat ttaaccctta gtttaagaag   4680
aagtcaatat gcttatttaa atattatgga tggtgggcag atcacttgag gtcaggagtt   4740
```

```
cgagaccagc ctggccaaca tggcaaaacc acatctctac taaaaataaa aaaattagct   4800

gggtgtggtg gtgcactcct gtaatcccag ctactcagaa ggctgaggta caagaattgc   4860

tggaacctgg gaggcggagg ttgcagtgaa ccaagattgc accactgcac tccagccggg   4920

gtgacagagt gagactccga ctgaaaataa ataaataaat aaataaataa ataaataaat   4980

attatggatg gtgaagggaa tggtatagaa ttggagagat tatcttactg aacacctgta   5040

gtcccagctt tctctggaag tggtcgtatt tgagcaggat gtgcacaagg caattgaaat   5100

gcccataatt agtttctcag ctttgaatac actataaact cactggctga aggaggaaat   5160

tttagaagga agctactaaa agatctaatt tgaaaaacta caaaagcatt aactaaaaaa   5220

gtttattttc cttttgtctg ggcagtagtg aaaataacta ctcacaacat tcactatgtt   5280

tgcaaggaat taacacaaat aaaagatgcc tttttactta aacaccaaga cagaaaactt   5340

gcccaatact gagaagcaac ttgcattaga gagggaactg ttaaatgttt tcaacccagt   5400

tcatctggtg gatgtttttg caggttactc tgagaatttt gcttatgaaa aatcattatt   5460

tttagtgtag ttcacaataa tgtattgaac atacttctaa tcaaaggtgc tatgtccttg   5520

tgtatggtac taaatgtgtc ctgtgtactt ttgcacaact gagaatcctg cagcttggtt   5580

taatgagtgt gttcatgaaa taaataatgg aggaattgtc a                     5621


<210> SEQ ID NO 8
<211> LENGTH: 3398
<212> TYPE: DNA
<213> ORGANISM: Homo sapiens
<300> PUBLICATION INFORMATION:
<308> DATABASE ACCESSION NUMBER: GenBank/NM_033102
<309> DATABASE ENTRY DATE: 2009-10-18
<313> RELEVANT RESIDUES IN SEQ ID NO: (1)..(3398)

<400> SEQUENCE: 8

aacctggaga tttaaaagcc gccggctggc gcgcgtgggg ggcaaggaag ggggggcgga     60

accagcctgc acgcgctggc tccgggtgac agccgcgcgc ctcggccagg atctgagtga    120

tgagacgtgt ccccactgag gtgcccccaca gcagcaggtg ttgagcatgg gctgagaagc    180

tggaccggca ccaaagggct ggcagaaatg ggcgcctggc tgattcctag gcagttggcg    240

gcagcaagga ggagaggccg cagcttctgg agcagagccg agacgaagca gttctggagt    300

gcctgaacgg ccccctgagc cctacccgcc tggcccacta tggtccagag gctgtgggtg    360

agccgcctgc tgcggcaccg gaaagcccag ctcttgctgg tcaacctgct aacctttggc    420

ctggaggtgt gtttggccgc aggcatcacc tatgtgccgc ctctgctgct ggaagtgggg    480

gtagaggaga agttcatgac catggtgctg ggcattggtc cagtgctggg cctggtctgt    540

gtcccgctcc taggctcagc cagtgaccac tggcgtggac gctatggccg ccgccggccc    600

ttcatctggg cactgtcctt gggcatcctg ctgagcctct ttctcatccc aagggccggc    660

tggctagcag ggctgctgtg cccggatccc aggcccctgg agctggcact gctcatcctg    720

ggcgtggggc tgctggactt ctgtggccag gtgtgcttca ctccactgga ggccctgctc    780

tctgacctct tccgggaccc ggaccactgt cgccaggcct actctgtcta tgccttcatg    840

atcagtcttg gggggctgcct gggctacctc ctgcctgcca ttgactggga caccagtgcc    900

ctggcccccct acctgggcac ccaggaggag tgcctctttg gcctgctcac cctcatcttc    960

ctcacctgcg tagcagccac actgctggtg gctgaggagg cagcgctggg ccccaccgag   1020

ccagcagaag ggctgtcggc cccctccttg tcgccccact gctgtccatg ccgggcccgc   1080
```

-continued

```
ttggctttcc ggaacctggg cgccctgctt ccccggctgc accagctgtg ctgccgcatg   1140
ccccgcaccc tgcgccggct cttcgtggct gagctgtgca gctggatggc actcatgacc   1200
ttcacgctgt tttacacgga tttcgtgggc gaggggctgt accagggcgt gcccagagct   1260
gagccgggca ccgaggcccg gagacactat gatgaaggcg ttcggatggg cagcctgggg   1320
ctgttcctgc agtgcgccat ctccctggtc ttctctctgg tcatggaccg gctggtgcag   1380
cgattcggca ctcgagcagt ctatttggcc agtgtggcag ctttccctgt ggctgccggt   1440
gccacatgcc tgtcccacag tgtggccgtg gtgacagctt cagccgccct caccgggttc   1500
accttctcag ccctgcagat cctgccctac acactggcct ccctctacca ccgggagaag   1560
caggtgttcc tgcccaaata ccgaggggac actggaggtg ctagcagtga ggacagcctg   1620
atgaccagct tcctgccagg ccctaagcct ggagctccct tccctaatgg acacgtgggt   1680
gctggaggca gtggcctgct cccacctcca cccgcgctct gcggggcctc tgcctgtgat   1740
gtctccgtac gtgtggtggt gggtgagccc accgaggcca gggtggttcc gggccggggc   1800
atctgcctgg acctcgccat cctggatagt gccttcctgc tgtcccaggt ggccccatcc   1860
ctgtttatgg gctccattgt ccagctcagc cagtctgtca ctgcctatat ggtgtctgcc   1920
gcaggcctgg gtctggtcgc catttacttt gctacacagg tagtatttga caagagcgac   1980
ttggccaaat actcagcgta gaaaacttcc agcacattgg ggtggagggc ctgcctcact   2040
gggtcccagc tccccgctcc tgttagcccc atggggctgc cgggctggcc gccagtttct   2100
gttgctgcca aagtaatgtg gctctctgct gccaccctgt gctgctgagg tgcgtagctg   2160
cacagctggg ggctggggcg tccctctcct ctctccccag tctctagggc tgcctgactg   2220
gaggccttcc aagggggttt cagtctggac ttatacaggg aggccagaag ggctccatgc   2280
actggaatgc ggggactctg caggtggatt acccaggctc agggttaaca gctagcctcc   2340
tagttgagac acacctagag aagggttttt gggagctgaa taaactcagt cacctggttt   2400
cccatctcta agccccttaa cctgcagctt cgtttaatgt agctcttgca tgggagtttc   2460
taggatgaaa cactcctcca tgggatttga acatatgaaa gttatttgta ggggaagagt   2520
cctgaggggc aacacacaag aaccaggtcc cctcagccca cagcactgtc tttttgctga   2580
tccacccccc tcttaccttt tatcaggatg tggcctgttg gtccttctgt tgccatcaca   2640
gagacacagg catttaaata tttaacttat ttatttaaca aagtagaagg gaatccattg   2700
ctagcttttc tgtgttggtg tctaatattt gggtagggtg ggggatcccc aacaatcagg   2760
tcccctgaga tagctggtca ttgggctgat cattgccaga atcttcttct cctggggtct   2820
ggccccccaa aatgcctaac ccaggacctt ggaaattcta ctcatcccaa atgataattc   2880
caaatgctgt tacccaaggt tagggtgttg aaggaaggta gagggtgggg cttcaggtct   2940
caacggcttc cctaaccacc cctcttctct tggcccagcc tggttccccc cacttccact   3000
cccctctact ctctctagga ctgggctgat gaaggcactg cccaaaattt cccctacccc   3060
caactttccc ctacccccaa ctttccccac cagctccaca accctgtttg gagctactgc   3120
aggaccagaa gcacaaagtg cggtttccca agcctttgtc catctcagcc cccagagtat   3180
atctgtgctt ggggaatctc acacagaaac tcaggagcac cccctgcctg agctaaggga   3240
ggtcttatct ctcagggggg gtttaagtgc cgtttgcaat aatgtcgtct tatttattta   3300
gcggggtgaa tattttatac tgtaagtgag caatcagagt ataatgttta tggtgacaaa   3360
attaaaggct ttcttatatg ttaaaaaaaa aaaaaaaa                           3398
```

<210> SEQ ID NO 9
<211> LENGTH: 19
<212> TYPE: DNA
<213> ORGANISM: Artificial Sequence
<220> FEATURE:
<223> OTHER INFORMATION: Forward primer for Hepsin

<400> SEQUENCE: 9
ccccaacagc gaggagaac 19

<210> SEQ ID NO 10
<211> LENGTH: 21
<212> TYPE: DNA
<213> ORGANISM: Artificial Sequence
<220> FEATURE:
<223> OTHER INFORMATION: Reverese primer for Hepsin

<400> SEQUENCE: 10
gggtagccag cacagaacat c 21

<210> SEQ ID NO 11
<211> LENGTH: 22
<212> TYPE: DNA
<213> ORGANISM: Artificial Sequence
<220> FEATURE:
<223> OTHER INFORMATION: Forward primer for TBP

<400> SEQUENCE: 11
gaatataatc ccaagcggtt tg 22

<210> SEQ ID NO 12
<211> LENGTH: 20
<212> TYPE: DNA
<213> ORGANISM: Artificial Sequence
<220> FEATURE:
<223> OTHER INFORMATION: Reverse primer for TBP

<400> SEQUENCE: 12
acttcacatc acagctcccc 20

<210> SEQ ID NO 13
<211> LENGTH: 20
<212> TYPE: DNA
<213> ORGANISM: Artificial Sequence
<220> FEATURE:
<223> OTHER INFORMATION: Forward primer for PSA

<400> SEQUENCE: 13
tgcccactgc atcaggaaca 20

<210> SEQ ID NO 14
<211> LENGTH: 21
<212> TYPE: DNA
<213> ORGANISM: Artificial Sequence
<220> FEATURE:
<223> OTHER INFORMATION: Reverse Primer for PSA

<400> SEQUENCE: 14
catcacctgg cctgaggaat c 21

<210> SEQ ID NO 15
<211> LENGTH: 20
<212> TYPE: DNA
<213> ORGANISM: Artificial Sequence
<220> FEATURE:
<223> OTHER INFORMATION: Forward primer for PCA3

<400> SEQUENCE: 15
tgtttttgca catttccagc 20

<210> SEQ ID NO 16
<211> LENGTH: 17
<212> TYPE: DNA
<213> ORGANISM: Artificial Sequence
<220> FEATURE:
<223> OTHER INFORMATION: Reverse primer for PCA3

<400> SEQUENCE: 16
gggcgaggct catcgat 17

<210> SEQ ID NO 17
<211> LENGTH: 21
<212> TYPE: DNA
<213> ORGANISM: Artificial Sequence
<220> FEATURE:
<223> OTHER INFORMATION: Forward primer for EZH2

<400> SEQUENCE: 17
gccagactgg gaagaaatct g 21

<210> SEQ ID NO 18
<211> LENGTH: 21
<212> TYPE: DNA
<213> ORGANISM: Artificial Sequence
<220> FEATURE:
<223> OTHER INFORMATION: Reverse Primer for EZH2

<400> SEQUENCE: 18
tgtgttggaa aatccaagtc a 21

<210> SEQ ID NO 19
<211> LENGTH: 20
<212> TYPE: DNA
<213> ORGANISM: Artificial Sequence
<220> FEATURE:
<223> OTHER INFORMATION: Forward primer for TRPM8

<400> SEQUENCE: 19
acgcttgtgt accggaatct 20

<210> SEQ ID NO 20
<211> LENGTH: 21
<212> TYPE: DNA
<213> ORGANISM: Artificial Sequence
<220> FEATURE:
<223> OTHER INFORMATION: Reverse primer for TRPM8

<400> SEQUENCE: 20
cgagtaatag gagacacgtc g 21

<210> SEQ ID NO 21
<211> LENGTH: 21
<212> TYPE: DNA
<213> ORGANISM: Artificial Sequence
<220> FEATURE:
<223> OTHER INFORMATION: Forward primer for Prostein

<400> SEQUENCE: 21
gccaggatct gagtgatgag a 21

<210> SEQ ID NO 22
<211> LENGTH: 20
<212> TYPE: DNA
<213> ORGANISM: Artificial Sequence
<220> FEATURE:
<223> OTHER INFORMATION: Reverse primer for Prostein

<400> SEQUENCE: 22
gttcaggcac tccagaactg 20

<210> SEQ ID NO 23
<211> LENGTH: 30
<212> TYPE: DNA
<213> ORGANISM: Artificial Sequence
<220> FEATURE:
<223> OTHER INFORMATION: Gene specific probe with fluorescein labeled 3'-End

<400> SEQUENCE: 23
gagtccccat aatcagcaat gatgtctgca 30

<210> SEQ ID NO 24
<211> LENGTH: 30
<212> TYPE: DNA
<213> ORGANISM: Artificial Sequence
<220> FEATURE:
<223> OTHER INFORMATION: Gene specific probe for Hepsin 5'-labeled with LCRed640

<400> SEQUENCE: 24
tggcgctgac ttctatggaa accagatcaa 30

<210> SEQ ID NO 25
<211> LENGTH: 25
<212> TYPE: DNA
<213> ORGANISM: Artificial Sequence
<220> FEATURE:
<223> OTHER INFORMATION: Gene specific probe for TBP 3'-labeled with Fluorescein

<400> SEQUENCE: 25
tttcccagaa ctgaaaatca gtgcc 25

<210> SEQ ID NO 26
<211> LENGTH: 26
<212> TYPE: DNA
<213> ORGANISM: Artificial Sequence
<220> FEATURE:
<223> OTHER INFORMATION: Gene specific probe for TBP 5'-labeled with LCRed640

<400> SEQUENCE: 26
tggttcgtgg ctctcttatc ctcatg 26

<210> SEQ ID NO 27
<211> LENGTH: 24
<212> TYPE: DNA
<213> ORGANISM: Artificial Sequence
<220> FEATURE:
<223> OTHER INFORMATION: Gene specific probe for PSA 3'-labeled with Fluorescein

<400> SEQUENCE: 27
atttcaggtc agccacagct tccc 24

<210> SEQ ID NO 28
<211> LENGTH: 25
<212> TYPE: DNA
<213> ORGANISM: Artificial Sequence
<220> FEATURE:
<223> OTHER INFORMATION: Gene specific probe for PSA 5'-labeled with LCRed640

<400> SEQUENCE: 28
cacccgctct acgatatgag cctcc 25

<210> SEQ ID NO 29
<211> LENGTH: 20
<212> TYPE: DNA
<213> ORGANISM: Artificial Sequence
<220> FEATURE:
<223> OTHER INFORMATION: Gene specific probe for PCA3 5'-labeled with 6-FAM

<400> SEQUENCE: 29
agaaatgccc ggccgccatc 20

<210> SEQ ID NO 30
<211> LENGTH: 25
<212> TYPE: DNA
<213> ORGANISM: Artificial Sequence
<220> FEATURE:
<223> OTHER INFORMATION: Gene specific probe for EZH2 3'-labeled with Fluorescein

<400> SEQUENCE: 30
aacctcttga gctgtctcag tcgca 25

<210> SEQ ID NO 31
<211> LENGTH: 25
<212> TYPE: DNA
<213> ORGANISM: Artificial Sequence
<220> FEATURE:
<223> OTHER INFORMATION: Gene specific probe for EZH2 5'-labeled with LCRed640

<400> SEQUENCE: 31
tactctgatt ttacacgctt ccgcc 25

<210> SEQ ID NO 32
<211> LENGTH: 24
<212> TYPE: DNA
<213> ORGANISM: Artificial Sequence
<220> FEATURE:
<223> OTHER INFORMATION: Gene specific probe for TRPM8 3'-labeled with Fluorescein

<400> SEQUENCE: 32
tttccagaca aacgtgagga gggc 24

<210> SEQ ID NO 33
<211> LENGTH: 27
<212> TYPE: DNA
<213> ORGANISM: Artificial Sequence
<220> FEATURE:
<223> OTHER INFORMATION: Gene specific probe for TRPM8 5'-labeled with LCRed640

<400> SEQUENCE: 33
cattatagga attcttggcg atctgca 27

```
<210> SEQ ID NO 34
<211> LENGTH: 20
<212> TYPE: DNA
<213> ORGANISM: Artificial Sequence
<220> FEATURE:
<223> OTHER INFORMATION: Gene specific fluorescent probe for prostein
      3'-labeled with Fluorescein

<400> SEQUENCE: 34

cggtccagct tctcagccca                                              20


<210> SEQ ID NO 35
<211> LENGTH: 22
<212> TYPE: DNA
<213> ORGANISM: Artificial Sequence
<220> FEATURE:
<223> OTHER INFORMATION: Gene specific probe for Prostein 5'-labeled
      with LCRed640

<400> SEQUENCE: 35

gctcaacacc tgctgctgtg gg                                           22


<210> SEQ ID NO 36
<211> LENGTH: 2389
<212> TYPE: DNA
<213> ORGANISM: Homo sapiens
<300> PUBLICATION INFORMATION:
<308> DATABASE ACCESSION NUMBER: GenBank/NM_182983
<309> DATABASE ENTRY DATE: 2009-07-18
<313> RELEVANT RESIDUES IN SEQ ID NO: (1)..(2389)

<400> SEQUENCE: 36

tcgagcccgc tttccaggga ccctacctga gggcccacag gtgaggcagc ctggcctagc     60

aggccccacg ccaccgcctc tgcctccagg ccgcccgctg ctgcggggcc accatgctcc    120

tgcccaggcc tggagactga cccgaccccg gcactacctc gaggctccgc ccccacctgc    180

tggaccccag ggtaaggaca agggccccca gactcacagt tccagccctg aggacagggg    240

ttccctcatc cccccaccca gcctaatgcc cacctcctaa tagaggggtt cctggggacc    300

tgaagagggg gcactatgac gtccccccaa gcacctaggt gttctgtcct gctcttcctt    360

cagactcagc cgttggaccc cagtcctttc ctccccagac ccaggagttc cagccctcag    420

gcccctcctc cctcatacta gggagtcctg gcccccaaat tcctcctttc ccaagactta    480

tgatttcagg tcctcagctg tctcctccct caaaccggga tcctcagtcc cctgctccac    540

caggctcagg catgggggtc cccatccctg caaatccagg cgtccccccg ctgctggtca    600

gacactgacc ccatccttga acccagccca atctgcgtcc gtgatcacgg cgtgctctgg    660

ccaaggccca gtccctacag cctgcctgga tggacgcctg ggactggggg cgccaggact    720

gggctgggct gggctccccc aggccctgcc tccccgtcca tctcctcaca ggtcccaccc    780

tggcccagga ggtcagccag ggaatcatta acaagaggca gtgacatggc gcagaaggag    840

ggtggccgga ctgtgccatg ctgctccaga cccaaggtgg cagctctcac tgcggggacc    900

ctgctacttc tgacagccat cggggcggca tcctgggcca ttgtggctgt tctcctcagg    960

agtgaccagg agccgctgta cccagtgcag gtcagctctg cggacgctcg gctcatggtc   1020

tttgacaaga cggaagggac gtggcggctg ctgtgctcct cgcgctccaa cgccagggta   1080

gccggactca gctgcgagga gatgggcttc ctcagggcac tgacccactc cgagctggac   1140

gtgcgaacgg cgggcgccaa tggcacgtcg ggcttcttct gtgtggacga ggggaggctg   1200

ccccacaccc agaggctgct ggaggtcatc tccgtgtgtg attgccccag aggccgtttc   1260

ttggccgcca tctgccaaga ctgtggccgc aggaagctgc ccgtggaccg catcgtggga   1320
```

```
ggccgggaca ccagcttggg ccggtggccg tggcaagtca gccttcgcta tgatggagca   1380
cacctctgtg gggatccct  gctctccggg gactgggtgc tgacagccgc ccactgcttc   1440
ccggagcgga accgggtcct gtcccgatgg cgagtgtttg ccggtgccgt ggcccaggcc   1500
tctccccacg gtctgcagct gggggtgcag gctgtggtct accacggggg ctatcttccc   1560
tttcgggacc ccaacagcga ggagaacagc aacgatattg ccctggtcca cctctccagt   1620
cccctgcccc tcacagaata catccagcct gtgtgcctcc cagctgccgg ccaggccctg   1680
gtggatggca agatctgtac cgtgacgggc tggggcaaca cgcagtacta tggccaacag   1740
gccggggtac tccaggaggc tcgagtcccc ataatcagca atgatgtctg caatggcgct   1800
gacttctatg gaaaccagat caagcccaag atgttctgtg ctggctaccc cgagggtggc   1860
attgatgcct gccagggcga cagcggtggt ccctttgtgt gtgaggacag catctctcgg   1920
acgccacgtt ggcggctgtg tggcattgtg agttggggca ctggctgtgc cctggcccag   1980
aagccaggcg tctacaccaa agtcagtgac ttccgggagt ggatcttcca ggccataaag   2040
actcactccg aagccagcgg catggtgacc cagctctgac cggtggcttc tcgctgcgca   2100
gcctccaggg cccgaggtga tcccggtggt gggatccacg ctgggcctag gatgggacgt   2160
ttttcttctt gggcccggtc cacaggtcca aggacaccct ccctccaggg tcctctcttc   2220
cacagtggcg ggcccactca gccccgagac cacccaacct caccctcctg acccccatgt   2280
aaatattgtt ctgctgtctg ggactcctgt ctaggtgccc ctgatgacgg gatgctcttt   2340
aaataataaa gatggttttg attaaaaaaa aaaaaaaaaa aaaaaaaaa               2389
```

<210> SEQ ID NO 37
<211> LENGTH: 1906
<212> TYPE: DNA
<213> ORGANISM: Homo sapiens
<300> PUBLICATION INFORMATION:
<308> DATABASE ACCESSION NUMBER: GenBank/NM_001030047
<309> DATABASE ENTRY DATE: 2009-12-06
<313> RELEVANT RESIDUES IN SEQ ID NO: (1)..(1906)

<400> SEQUENCE: 37

```
agccccaagc ttaccacctg cacccggaga gctgtgtcac catgtgggtc ccggttgtct     60
tcctcaccct gtccgtgacg tggattggtg ctgcacccct catcctgtct cggattgtgg    120
gaggctggga gtgcgagaag cattcccaac cctggcaggt gcttgtggcc tctcgtggca    180
gggcagtctg cggcggtgtt ctggtgcacc cccagtgggt cctcacagct gcccactgca    240
tcaggaacaa aagcgtgatc ttgctgggtc ggcacagcct gtttcatcct gaagacacag    300
gccaggtatt tcaggtcagc cacagcttcc cacacccgct ctacgatatg agcctcctga    360
agaatcgatt cctcaggcca ggtgatgact ccagccacga cctcatgctg ctccgcctgt    420
cagagcctgc cgagctcacg gatgctgtga aggtcatgga cctgcccacc caggagccag    480
cactggggac cacctgctac gcctcaggct ggggcagcat tgaaccagag gagttcttga    540
ccccaaagaa acttcagtgt gtggacctcc atgttatttc caatgacgtg tgtgcgcaag    600
ttcaccctca gaaggtgacc aagttcatgc tgtgtgctgg acgctggaca gggggcaaaa    660
gcacctgctc gtgggtcatt ctgatcaccg aactgaccat gccagccctg ccgatggtcc    720
tccatggctc cctagtgccc tggagaggag gtgtctagtc agagagtagt cctggaaggt    780
ggcctctgtg aggagccacg gggacagcat cctgcagatg gtcctggccc ttgtcccacc    840
gacctgtcta caaggactgt cctcgtggac cctcccctct gcacaggagc tggaccctga    900
agtcccttcc ccaccggcca ggactggagc ccctacccct ctgttggaat ccctgcccac    960
```

```
cttcttctgg aagtcggctc tggagacatt tctctcttct tccaaagctg ggaactgcta   1020
tctgttatct gcctgtccag gtctgaaaga taggattgcc caggcagaaa ctgggactga   1080
cctatctcac tctctccctg cttttaccct tagggtgatt ctgggggccc acttgtctgt   1140
aatggtgtgc ttcaaggtat cacgtcatgg ggcagtgaac catgtgccct gcccgaaagg   1200
ccttccctgt acaccaaggt ggtgcattac cggaagtgga tcaaggacac catcgtggcc   1260
aacccctgag cacccctatc aacccctat tgtagtaaac ttggaacctt ggaaatgacc   1320
aggccaagac tcaagcctcc ccagttctac tgacctttgt ccttaggtgt gaggtccagg   1380
gttgctagga aaagaaatca gcagacacag gtgtagacca gagtgtttct taaatggtgt   1440
aattttgtcc tctctgtgtc ctggggaata ctggccatgc ctggagacat atcactcaat   1500
ttctctgagg acacagatag gatggggtgt ctgtgttatt tgtggggtac agagatgaaa   1560
gaggggtggg atccacactg agagagtgga gagtgacatg tgctggacac tgtccatgaa   1620
gcactgagca gaagctggag gcacaacgca ccagacactc acagcaagga tggagctgaa   1680
aacataaccc actctgtcct ggaggcactg ggaagcctag agaaggctgt gagccaagga   1740
gggagggtct tcctttggca tgggatgggg atgaagtaag gagagggact ggaccccctg   1800
gaagctgatt cactatgggg ggaggtgtat tgaagtcctc cagacaaccc tcagatttga   1860
tgatttccta gtagaactca cagaaataaa gagctgttat actgtg                  1906
```

<210> SEQ ID NO 38
<211> LENGTH: 1341
<212> TYPE: DNA
<213> ORGANISM: Homo sapiens
<300> PUBLICATION INFORMATION:
<308> DATABASE ACCESSION NUMBER: GenBank/NM_001030049
<309> DATABASE ENTRY DATE: 2009-12-06
<313> RELEVANT RESIDUES IN SEQ ID NO: (1)..(1341)

<400> SEQUENCE: 38

```
agccccaagc ttaccacctg cacccggaga gctgtgtcac catgtgggtc ccggttgtct     60
tcctcaccct gtccgtgacg tggattggtg ctgcacccct catcctgtct cggattgtgg    120
gaggctggga gtgcgagaag cattcccaac cctggcaggt gcttgtggcc tctcgtggca    180
gggcagtctg cggcggtgtt ctggtgcacc cccagtgggt cctcacagct gcccactgca    240
tcaggaacaa aagcgtgatc ttgctgggtc ggcacagcct gtttcatcct gaagacacag    300
gccaggtatt tcaggtcagc cacagcttcc cacacccgct ctacgatatg agcctcctga    360
agaatcgatt cctcaggcca ggtgatgact ccagcattga accagaggag ttcttgaccc    420
caaagaaact tcagtgtgtg gacctccatg ttatttccaa tgacgtgtgt gcgcaagttc    480
accctcagaa ggtgaccaag ttcatgctgt gtgctggacg ctggacaggg ggcaaaagca    540
cctgctcggg tgattctggg ggcccacttg tctgtaatgg tgtgcttcaa ggtatcacgt    600
catggggcag tgaaccatgt gccctgcccg aaaggccttc cctgtacacc aaggtggtgc    660
attaccggaa gtggatcaag gacaccatcg tggccaaccc ctgagcaccc ctatcaaccc    720
cctattgtag taaacttgga accttggaaa tgaccaggcc aagactcaag cctccccagt    780
tctactgacc tttgtcctta ggtgtgaggt ccagggttgc taggaaaaga aatcagcaga    840
cacaggtgta gaccagagtg tttcttaaat ggtgtaattt tgtcctctct gtgtcctggg    900
gaatactggc catgcctgga gacatatcac tcaatttctc tgaggacaca gataggatgg    960
ggtgtctgtg ttatttgtgg ggtacagaga tgaaagaggg gtgggatcca cactgagaga   1020
gtggagagtg acatgtgctg gacactgtcc atgaagcact gagcagaagc tggaggcaca   1080
```

-continued

```
acgcaccaga cactcacagc aaggatggag ctgaaaacat aacccactct gtcctggagg   1140

cactgggaag cctagagaag gctgtgagcc aaggagggag ggtcttcctt tggcatggga   1200

tggggatgaa gtaaggagag ggactggacc ccctggaagc tgattcacta tgggggggagg   1260

tgtattgaag tcctccagac aaccctcaga tttgatgatt tcctagtaga actcacagaa   1320

ataaagagct gttatactgt g                                            1341
```

NON-INVASIVE METHOD FOR DIAGNOSIS OF PROSTATE CANCER

CROSS-REFERENCE TO RELATED APPLICATIONS

Figure 1:
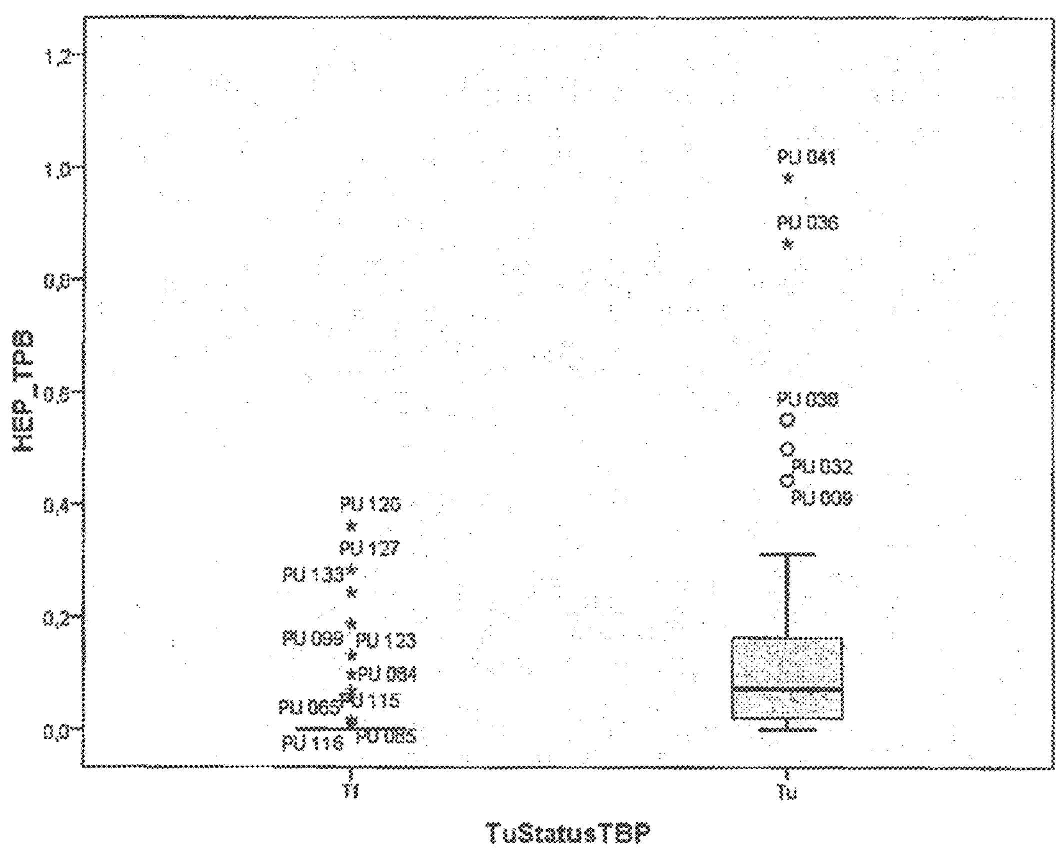

This application is a National Stage of PCT/EP2010/069810, filed Dec. 15, 2010 which claims priority to European Application No. 09179327.3, flied Dec. 15, 2009, the disclosures of which are incorporated herein by reference in their entireties.

FIELD OF THE INVENTION

Subject of the present invention is a non-invasive method for diagnosis of prostate cancer or the assessment of the risk of a subject to acquire prostate cancer. Particularly by determining the presence of at least hepsin in urine samples.

BACKGROUND OF THE INVENTION

Prostate cancer is a form of cancer that develops in the prostate. Prostate cancer may cause difficulties in urinating, pain, problems during sexual intercourse, or erectile dysfunction. Moreover, the cancer cells may metastasize (spread) from the prostate to other parts of the body, particularly the lymph nodes and bones subsequently leading to pain in the back and the bones. Prostate cancer tends to develop in men over the age of fifty and it is one of the most prevalent types of cancer in men. Development of prostate cancer is influenced by many factors, including genetics and diet.

Atypical adenomatous hyperplasia (AAH) is a term that has been utilized to describe changes histologically seen in prostatic glands in the apex, periurethral region, and/or transition zone of the prostate. AAH is a localized proliferation of small acini within the prostate. Such proliferations may be confused with carcinoma, but the glands with AAH still have a fragmented basal layer. AAH can be difficult to distinguish from hyperplasia. There is a association between the presence of AAH and the development of prostate cancer.

Prostatic intraepithelial neoplasia (PIN), which is dysplasia of the epithelium lining prostate glands, is a probable precursor of prostate cancer. The appearance of PIN may precede carcinoma by 10 or more years. It can be divided into low grade and high grade PIN. Low grade PIN may be found even in men in middle age. PIN is characterized histologically by progressive basal cell layer disruption, loss of markers of secretory differentiation, nuclear and nucleolar abnormalities, increasing proliferative potential, increasing microvessel density, variation in DNA content, and allelic loss. Unlike prostate cancer, with which it may coexist, glands with PIN retain an intact or fragmented basal cell layer.

The appearance of PIN, in particular of high-grade PIN (HG-PIN) warrants increased surveillance of the prostate for development of an invasive carcinoma because the presence of HG-PIN suggests an increased risk for subsequent appearance of prostate cancer. Since HG-PIN lesions are also associated with the presence of cancer in many patients, men whose biopsies show HG-PIN are often re-biopsied until cancer is detected.

Today the only test that can fully confirm the diagnosis of prostate cancer is a biopsy, the removal of small pieces of the prostate for microscopic examination. However, prior to a biopsy, several other tools are used to gather more information about the prostate and the urinary tract before conducting this invasive method. Prostate cancers may be detected by digital examination, by transrectal ultrasonography, or by screening with a serum test for prostate specific antigen (PSA). None of these methods can reliably detect all prostate cancers, particularly the small cancers. However, if cancer is suspected, a biopsy is offered. During a biopsy a tissue sample from the prostate is obtained via the rectum. A biopsy gun inserts and removes special hollow-core needles (usually three to six on each side of the prostate). The procedure requires a local anaesthetic, and is associated with frequent complications, e.g. bleeding in the urine, bleeding in the stool, blood in the ejaculate and soreness in the biopsied area afterwards. Most men report discomfort during prostate biopsy (Essink-Bot, M L et al. J Natl Cancer Inst 90: 925-31). The tissue samples are then examined under a microscope to determine histopathologically whether cancer cells are present, and to evaluate the morphologic features (Gleason score) of any cancer found (Gleason D F. in Tannenbaum M (ed.) Urologic Pathology: The Prostate. Lea and Febiger, Philadelphia, 1977; 171-198).

Hepsin (HPN/TMPRSS1 (GeneID 3249); mRNA (NM_002151; SEQ ID NO. 1) or (NM_182983; SEQ ID NO. 36)) is a membrane serine protease that is highly expressed in prostate tissue. Expression profiling studies of mRNA have also shown an over-expression of hepsin in 90% of the analyzed prostate cancers (Stephan et al. 2004; J Urol.; 171(1): 187-91). Another study using immunohistochemistry showed hepsin to be highly produced in PIN lesions and to be preferentially produced in prostate cancer compared with benign prostatic hyperplasia (BPH) (Dhanasekaran et al 2001). However, the lack of detection of hepsin in blood, serum or urine limits its role as a biomarker so far (Parekh et al. 2007; J Urol.; 178(6):2252-9; Sardana et al. 2008 Clin Chem.; 54(12):1951-60; Kelly et al. 2008. Cancer Res.; 68(7):2286-91; Morrissey et al. 2008, Clin Exp Metastasis; 25(4):377-88.)

At present, an active area of research involves non-invasive methods of prostate cancer detection. A method of early prostate tumor detection is a test for the presence of cell-associated PCA3 (prostate cancer antigen 3, formerly DD3, GeneID 50652, non-coding RNA NR_015342 (SEQ ID NO. 4) or RNA AF103907 (SEQ ID NO. 5)) mRNA in urine. PCA3 mRNA is expressed almost exclusively by prostate cells and has been shown to be highly over-expressed in prostate cancer cells. Thus, PCA3 is an additional tool to help decide whether, in men suspected of having prostate cancer, a biopsy is really needed. The higher the concentration of PCA3 in urine, the greater the likelihood of a positive biopsy, i.e. the presence of cancer cells in the prostate. However, the disadvantages of this method are the still unsatisfactory rates for sensitivity and specificity (Kirby et al. 2009; BJU Int.; 103(4):441-5.).

A further commonly used test to asses the presence of prostate cancer is the Prostate Specific Antigen (PSA) (kallikrein-related peptidase 3, KLK3, GeneID 354, mRNA transcript variant 1 NM_001648 (SEQ ID NO. 3) or transcript variant 3 NM_001030047 (SEQ ID NO. 37 or transcript variant 5 NM_001030049 (SEQ ID NO. 38)) test. The PSA test measures the blood level of prostate-specific antigen, an enzyme produced by the prostate. Increased PSA levels correlate with an increased risk for prostate cancer (Cataluna W J. "How I manage a patient with a newly elevated PSA", 2007, CDC Cancer Conference. http://www.cdccancerconference.net/Presentations/ET2.0/ET2.0_Catalona.pdf). 4 ng/mL was chosen arbitrarily as a decision level for biopsies in the clinical trial upon which the FDA in 1994 based adding prostate cancer detection in men age 50 and over as an approved indication for the first commercially available PSA test. 4 ng/mL was used as the biopsy decision level in the PLCO trial, 3 ng/mL was used in the ERSPC and ProtecT trials, and 2.5 ng/mL is used in the 2007 NCCN guideline.

PSA levels can change for many reasons other than cancer. Two common causes of high PSA levels are enlargement of the prostate (BPH) and inflammation in the prostate (prostatitis). It can also be raised for 24 hours after ejaculation and several days after catheterization. Even though widely used, PSA levels can not alone be a reliable marker for diagnosis of prostate cancer.

Regardless by which test the probability of the presence of prostate cancer is determined, the diagnosis has to be confirmed by taking a biopsy of the prostate and examining it under a microscope.

Thus, there is need for a reliable, non-invasive method for the diagnosis of prostate cancer which affords both, sensitivity and specificity, i.e. minimizing false positive and false negative diagnosis.

DESCRIPTION OF THE INVENTION

The inventors surprisingly found a significant correlation between the presence of hepsin mRNA (NM_002151 (SEQ ID NO. 1) or NM_182983 (SEQ ID NO. 36) in a urine sample preferentially in one embodiment derived from a subject after digital-rectal-examination and the presence of prostate cancer or atypical adenomatous hyperplasia, which may result in prostate cancer.

Digital rectal examination (DRE) is a procedure where the examiner inserts a gloved, lubricated finger into the rectum to check the size, shape, and texture of the prostate. Usually a DRE is conducted in the following way: The physician feels the back surface of the prostate gland for any hard or irregular areas and to estimate its size. A regular DRE comprises about 3 strokes per lobe, from the base to the apex and from the lateral to the median line. If the prostate gland is larger than expected this could be a sign of BPH. A prostate gland with hard bumpy areas may suggest prostate cancer.

Thus, the present invention relates on a non-invasive method for diagnosing prostate cancer and/or assessing the risk of a subject acquiring prostate cancer comprising the analysis of the expression of the marker gene hepsin in an urine sample, wherein the analysis comprises the steps of (i) determining hepsin (HPN/TMPRSS1 (GeneID 3249), mRNA (NM_002151 (SEQ ID NO. 1) and/or NM_182983 (SEQ ID NO. 36)) in said urine sample; and (ii) attributing the presence of hepsin to the diagnosis of prostate cancer in said subject and/or an increased risk of said subject for acquiring prostate cancer, wherein said urine sample is obtained from said subject after digital-rectal-examination of said subject.

The inventors found that the specificity of the method according to the invention may be increased when the expression level of hepsin is determined, i.e. the concentration of a gene product of the hepsin gene is determined in said urine sample. Thus, in a preferred embodiment the present invention also encompasses a non-invasive method for diagnosing prostate cancer and/or assessing the risk of a subject for acquiring prostate cancer, wherein the analysis of the expression of hepsin in said urine sample comprises the following steps of (i) determining the expression level of hepsin in said urine sample; (ii) determining the expression level of at least one reference gene in said urine sample; (iii) normalizing the expression level of the marker gene, wherein the at least one reference gene is characterized by a constant expression in prostate cells independent of the presence of prostate cancer; and (iv) attributing the normalized expression level of the marker gene to the diagnosis of prostate cancer in said subject and/or an increased risk of said subject acquiring prostate cancer.

A reference gene according to the present invention is characterized by constant expression level when comparing the expression levels of said reference gene in urine samples taken directly after a DRE from individuals having prostate cancer with the expression levels of said reference gene in urine samples taken from individuals not having prostate cancer. Constant expression level means that the relative amount of a gene product of said reference gene compared to the total analyzed sample material in the sample does not change significantly. The total analyzed sample material may be determined by the total volume of the analyzed urine sample and/or the amount of cells contained therein and/or the total amount of RNA and/or DNA and/or the total protein content.

The term "gene product" as used herein refers to a protein encoded by a gene or a RNA transcribed from a gene, e.g. mRNA.

The term "normalizing" as used herein, in reference to the comparison of the expression level of a marker gene to the expression level of a reference gene. By comparison according to the present invention it is meant that the relative amount of molecules in a sample is calculated, e.g. transcripts of the marker gene per transcripts of the reference gene. Methods of normalizing expression levels are known by the skilled artisan.

The inventors found that for the purpose of the method according to the present invention the TATA-Box-binding protein (TBP) (mRNA (NM_003194); SEQ ID NO. 2) is a very reliable reference gene. Thus, in a preferred embodiment of the present invention TBP is used as the at least one reference gene according to the invention. However, the skilled artisan will unambiguously recognize that also other so called housekeeping genes are well suited as reference genes. The term housekeeping gene in the context of the present invention refers to genes, which are constitutively expressed at a relatively constant level across many or all known conditions. They code for proteins that are generally involved in the basic functions necessary for the sustenance or maintenance of the cell. Thus, in a further preferred embodiment the reference gene is selected from the group consisting of TATA-Box binding protein (TBP), HPRT1 (hypoxanthine phosphoribosyltransferase 1), HMBS=PBGD (hydroxymethylbilane synthase or porphobilinogen deaminase), PPIA (peptidylprolyl isomerase A), GAPDH (glyceraldehyde-3-phosphate dehydrogenase), ACTB (beta actin), G6PD (glucose-6-phosphate dehydrogenase), ALAS1 (Delta-aminolevulinate synthase 1), SDHA (succinate dehydrogenase complex flavoprotein subunit A).

Furthermore, the inventors found that the reliability of the diagnostic method according to the invention is further increased when in addition to the expression level of hepsin the expression level of prostate cancer antigen 3 (PCA3, GeneID 50652; non-coding RNA NR_015342 (SEQ ID NO. 4), and/or non coding RNA AF103907 (SEQ ID NO. 5)) and the prostate specific antigen (PSA, KLK3, GeneID 354; mRNA NM_001648 (SEQ ID NO. 3) and/or NM_001030047 (SEQ ID NO. 37 and/or NM_001030049 (SEQ ID NO. 38)), or the expression levels of PCA3, enhancer of zeste homolog 2 gene (EZH2, GeneID 2146; mRNA NM_004456 (SEQ ID NO. 6)), transient receptor potential cation channel, subfamily M, member 8 (TRPM8, GeneID 79054; mRNA NM_024080 (SEQ ID NO. 7)) and prostein (solute carrier family 45, member 3, SLC45A3, GeneID 85414, mRNA NM_033102 (SEQ ID NO. 8)); or the expression level of PCA3 (SEQ ID NO. 4), EZH2 (SEQ ID NO. 6) and prostein (SEQ ID NO. 8) are analyzed. Thus, in a preferred embodiment the expression levels PCA3 (SEQ ID NO. 4) and PSA (SEQ ID NO. 3 and/or SEQ ID NO. 37 and/or SEQ ID NO. 38) are analyzed in addition to the expression level of hepsin (SEQ ID NO. 1 and/or SEQ ID NO. 36) in the method according to the present invention. In a further preferred embodiment the expression levels of the marker genes PCA3 (SEQ ID NO. 4), EZH2 (SEQ ID NO. 6), TRPM8 (SEQ ID NO. 7) and prostein (SEQ ID NO. 8) are analyzed in addition to the expression level of hepsin (SEQ ID NO. 1 and/or SEQ ID NO. 36) in the method according to the present invention. In a particularly preferred embodiment the expression levels of the marker genes PCA3 (SEQ ID NO. 4), EZH2 (SEQ ID NO. 6) and prostein (SEQ ID NO. 8) are analyzed in addition to the expression level of hepsin (SEQ ID NO. 1 and/or SEQ ID NO. 36) in the method according to the present invention.

It was surprisingly found that the expression levels of the marker gene(s) according to the present invention were also increased in urine samples from patient not yet suffering from prostate cancer but having an AAH. Thus, the method according to the present invention relates also on the assessment of the risk of a subject to acquire prostate cancer. In a preferred embodiment the method according to the present invention is used to acquire the risk of a subject to acquire prostate cancer by diagnose the presence of a prostate cancer precursor, like AAH, and/or HG-PIN.

The expression levels of the marker gene(s) as obtained by the methods or the use of the methods according to the present invention may be analyzed in a number of fashions well known to a person skilled in the art. For example, each assay result obtained may be compared to a "normal" value, or a value indicating a particular disease or outcome. A particular diagnosis/prognosis may depend upon the comparison of each assay result to such a value, which may be referred to as a diagnostic or prognostic "threshold". In certain embodiments, assays for one or more diagnostic or prognostic indicators are correlated to a condition or disease by merely the presence or absence of the indicator(s) in the assay. For example, an assay can be designed so that a positive signal only occurs above a particular threshold concentration of interest, and below which concentration the assay provides no signal above background.

The term "attributing", as used herein in reference to the use of marker gene(s), refers to comparing the presence or expression level of the marker gene(s) in the urine sample to its presence and/or expression level in urine samples derived from subjects known to suffer from, or known to be at risk of a given condition; or in urine sample from a subject known to be free of a given condition. The expression level(s) of marker gene(s) in a urine sample of a subject can be compared to an expression level known to be associated with a specific diagnosis. The expression level of a marker gene is said to have been correlated with a diagnosis, that is, the skilled artisan can use the expression level to determine whether the patient suffers from a specific type diagnosis, and respond accordingly. Alternatively, the expression level can be compared to a marker level known to be associated with a good outcome (e.g., the absence of disease, etc.). In preferred embodiments, a panel of expression levels of marker genes is correlated to a global probability or a particular outcome.

For any particular marker, the distributions of marker levels for subjects with and without a disease will likely overlap. Under such conditions, a diagnostic and/or prognostic test does not absolutely distinguish normal from disease with 100% accuracy, and the area of overlap indicates where the test cannot distinguish normal from disease. The sensitivity and specificity of such a test depends on more than just the analytical "quality" of the test, they also depend on the definition of what constitutes a test positive result. A test positive result is given if the measure value of the test is within an "abnormal" range which is separated by a threshold. A threshold is selected, above which (or below which, depending on how a marker changes with the disease) the test is considered to be abnormal and below which the test is considered to be normal. Sensitivity and specificity of the test result by fixing the threshold. By varying the threshold, sensitivity and specificity change reversal. The final used threshold depends on the clinical aims of the diagnostic or prognostic procedure. In the screening situation, the aim consists in the detection of possible great part of the patients with disease by a threshold with high sensitivity, but a low specificity is connected with that. Vice versa, a test with a high specificity is connected with a low sensitivity. Therefore, sensitivity and specificity are not suitable for a comparison of different quantitative tests. Alternative, the Receiver Operating Characteristic curves (ROC curves) are used. The horizontal axis of the ROC curve represents (1-specificity), which increases with the rate of false positives. The vertical axis of the curve represents sensitivity, which increases with the rate of true positives. Thus, for a particular cut-off selected, the value of (1-specificity) may be determined, and a corresponding sensitivity may be obtained. The area under the ROC curve (AUC) is a measure of the probability that the measured marker level will allow correct identification of a disease or condition independent from the threshold and from the clinical aim of the diagnostic or prognostic procedure. Thus, the area under the ROC curve (AUC) value can be used to determine the effectiveness of the test and to compare different tests. An AUC of 0.5 corresponds with the result of a dice game. The higher the AUC the higher is the goodness of the test.

Preferably, a threshold is selected to provide a ROC curve area of greater than about 0.5, preferably greater than about 0.6, more preferably greater than about 0.65, still more preferably 0.7, even more preferably greater than about 0.8, and most preferably greater than about 0.9. The term "about" in this context refers to +/−5% of a given measurement.

In certain embodiments, particular thresholds for one or more markers in a panel are not relied upon to determine if a profile of marker levels obtained from a subject are indicative of a particular diagnosis/prognosis. Rather, the present invention may utilize an evaluation of a marker panel "profile" as a unitary whole. A particular "fingerprint" pattern of changes in such a panel of markers may, in effect, act as a specific diagnostic or prognostic indicator. A panel herein refers to a set of marker genes. A preferred set of markers according to the present invention comprises hepsin, PCA3 and PSA. A further preferred set of marker genes comprises hepsin, PCA3, EZH2, TRPM8 and prostein. A further particularly preferred set of marker genes according to the present invention comprises PCA3, EZH2, prostein and hepsin.

As described herein after, a panel response value is preferably determined by plotting ROC curves for the sensitivity (i.e. true positives) of a particular panel of markers versus 1-(specificity) (i.e. false positives) for the panel at various cut-offs. In these methods, a profile of marker measurements from a subject is considered together to provide a global probability (expressed either as a numeric score or as a percentage risk) of a diagnosis or prognosis. In such embodiments, an increase in a certain subset of markers may be sufficient to indicate a particular diagnosis/prognosis in one patient, while an increase in a different subset of markers may be sufficient to indicate the same or a different diagnosis/ prognosis in another patient. Weighting factors may also be applied to one or more markers in a panel, for example, when a marker is of particularly high utility in identifying a particular diagnosis/prognosis, it may be weighted so that at a given level it alone is sufficient to signal a positive result. Likewise, a weighting factor may provide that no given level of a particular marker is sufficient to signal a positive result, but only signals a result when another marker also contributes to the analysis.

In certain embodiments, markers and/or marker panels are selected to exhibit at least about 70% sensitivity, more preferably at least about 80% sensitivity, even more preferably at least about 85% sensitivity, still more preferably at least about 90% sensitivity, and most preferably at least about 95% sensitivity, combined with at least about 70% specificity, more preferably at least about 80% specificity, even more preferably at least about 85% specificity, still more preferably at least about 90% specificity, and most preferably at least about 95% specificity. In a particularly preferred embodiment the markers and/or marker panels are selected to exhibit at least about 99% sensitivity. In further preferred embodiments, both the sensitivity and specificity are at least about 75%, more preferably at least about 80%, even more preferably at least about 85%, still more preferably at least about 90%, and most preferably at least about 95%. In a particularly preferred embodiment the markers and/or marker panels are selected to exhibit at least about 99% sensitivity and specificity. The term "about" in this context refers to +/−5% of a given measurement.

Further measures for comparisons of different diagnostic or prognostic tests in defined clinical situations and aims are the positive and negative predictive values (post test values). The positive predictive value (ppv) gives the conditioned probability that a patient with test positive result has the searched disease. Thus, ppv is the certainty of diagnosis. The negative predictive value (npv) gives the conditioned probability that a patient with test negative result has not the searched disease. Thus, npv is the certainty of exclusion of diagnosis. Both depend on the certainty of diagnosis before using the test (pretest value) and thus from the case mix in the clinical clientele.

Further measures for comparisons of different diagnostic or prognostic tests are the Likelihood Ratios ($LR_+$ and $LR_-$). They are measures of multiplicative changes of the odds for disease and exclusion of disease before and after using the test. In comparison to ppv and npv, these measures have the advantages of independence from the pretest odds and thus they are independent from the case mix in the clinical clientele. $LR_+$ is the factor for the pretest odds of the searched disease. A value of 1 indicates that the test does not give an information on the presence of the disease. Values greater than 1 show the increase of the certainty of diagnosis. $LR_-$ is the factor for the pretest odds of exclusion of the searched disease. A value of 1 indicates that the test does not give an information over the absence of the disease. Values greater than 1 shows the increase of the certainty of exclusion of diagnosis. Some authors use the inverse of $LR_-$. The likelihood ratios are the best suitable measures for the comparisons of quantitative diagnostic or prognostic tests. In certain preferred embodiments, markers and/or marker panels are preferably selected to exhibit a positive or negative likelihood ratio of at least about 1.5 or more or about 0.92 or less, more preferably at least about 2 or more or about 0.5 or less, still more preferably at least about 5 or more or about 0.2 or less, even more preferably at least about 10 or more or about 0.1 or less, and most preferably at least about 20 or more or about 0.05 or less. The term "about" in this context refers to +/−5% of a given measurement.

Another statistical method to access the probability of an outcome known by the skilled artisan is the logistic regression (Agresti, Alan. (2002). Categorical Data Analysis. New York: Wiley-Interscience; Amemiya, T. (1985). Advanced Econometrics. Harvard University Press; Balakrishnan, N. (1991). Handbook of the Logistic Distribution. Marcel Dekker, Inc, Greene, William H. (2003). Econometric Analysis, fifth edition. Prentice Hall; Hilbe, Joseph M. (2009). Logistic Regression Models. Chapman & Hall/CRC Press; Hosmer, David W.; Stanley Lemeshow (2000). Applied Logistic Regression, 2nd ed. New York; Chichester, Wiley. ISBN 0-471-35632-8).

Logistic regression models reproduce the relation between several explanatory variables and a binary dependent variable using stochastic characteristics and models. They serve e.g. to an individual diagnosis, prognosis, and decision-making. They estimate the logit (=log of odds) of one of the two values of the dependent variable for a single individual by a linear combination of all independent variables. In our case, the use of logistic regression models results in an estimation of the absolute probability for the existence of disease at a single patient which is equivalent to the certainty of diagnosis. Such models are the result of the search to optimal description of the nonlinear association between the existence and non-existence of the disease and one or more quantitative markers. Multivariate logit models results from stepwise model choice in which markers and their nonlinear transformations are included or excluded from the model corresponding to their diagnostic information in the corresponding step. Thus, not all primary markers are included in the optimal model. Some criterions for statistical optimality and validity have been given before such a model can be published and can be used. The logit model is valid only for the same case mix of patients with and without the searched disease in the concrete clinical situation as given in the diagnostic study. The diagnostic or prognostic goodness describes the AUC of the ROC similar to the single original diagnostic marker. Different to the last, the ROC results in this occasion by varying the threshold for the predicted probability for the existence of the disease in "high" and "not high". Logistic regression models are well researched and well established regarding statistical and epidemiological theory. Tables for the regressions coefficients and their statistical characteristics describe a concrete logit model and the accompanying rules for the computation of the certainty of diagnosis. For a concrete patient, the value of the logit has to be calculated by multiplying the measured values of the markers with the accompanying regression coefficients and by the sum of all parts. The searched certainty of diagnosis results from the calculated sum of logits by the transformation exp(sum of logits)/exp(sum of logits).

The skilled artisan will understand that associating a diagnostic or prognostic indicator, with a diagnosis or with a prognostic risk of a future clinical outcome is a statistical analysis. For example, a marker level of greater than X may signal that a patient is more likely to suffer from an adverse outcome than patients with a level less than or equal to X, as determined by a level of statistical significance. Additionally, a change in marker concentration from baseline levels may be reflective of patient prognosis, and the degree of change in marker level may be related to the severity of adverse outcome. Statistical significance is often determined by comparing two or more populations, and determining a confidence interval and/or a p value (see, e.g., Dowdy and Wearden, *Statistics for Research*, John Wiley & Sons, New York, 1983). Preferred confidence intervals of the invention are 90%, 95%, 97.5%, 98%, 99%, 99.5%, 99.9% and 99.99%, while preferred p values are 0.1, 0.05, 0.025, 0.02, 0.01, 0.005, 0.001, and 0.0001.

In yet other embodiments, multiple determinations of diagnostic or prognostic markers can be made, and a temporal change in the marker can be used to determine a diagnosis or prognosis. For example, a marker concentration in a subject sample may be determined at an initial time, and again at a second time from a second subject sample. In such embodiments, an increase in the marker from the initial time to the second time may be indicative of a particular diagnosis, or a particular prognosis. Likewise, a decrease in the marker from the initial time to the second time may be indicative of a particular diagnosis, or a particular prognosis.

The most preferred thresholds for the marker genes normalized to TBP as reference gene are given in Table 4. In context with the present invention normalized expression levels of the marker genes mentioned herein the respective thresholds are associated with an increased likelihood for the presence of prostate cancer and/or an increased risk of the subject for acquiring prostate cancer. Thus, in a preferred embodiment normalized expression levels of more than 0, preferably more than 0.01, more preferably more than 0.0168 for hepsin; and/or a normalized expression level of more 10, preferably more than 12, more preferably more than 14.32 for PSA; and/or a normalized expression level of less than 0.6, preferably less than 0.4, more preferably less than 0.21 for prostein; and/or a normalized expression level of more than 0.2, preferably more than 0.4, more preferably more than 0.58 for TRPM8; and/or a normalized expression level of less than 3, preferably less than 2, more preferably less than 1.87 for EZH2; and/or a normalized expression level of more than 1 for PCA3, preferably more than 2, more preferably more than 2.15 for PCA3 are attributed to an increased likelihood for the presence of prostate cancer in said patient and/or an increased risk of said subject for acquiring prostate cancer. Methods and means for assessing the expression level of a gene are well known to the skilled artisan. The methods and means used in analyzing the expression of the marker genes and/or reference genes according to the invention are dependent on the type of molecules which shall be detected and/or quantified.

In a preferred embodiment the expression level of the marker gene(s) and/or the at least one reference gene according to the present invention is determined by the quantification of transcripts. Methods for quantification of transcripts, e.g. mRNA, are well known in the art. One widely established quantification method is the quantitative reverse transcription real-time PCR. Thus, in a preferred embodiment of the present invention the expression levels of said marker gene(s) and said at least one reference gene is determined by quantitative reverse transcription real-time PCR (q-RT PCR).

Quantitative reverse transcription real-time PCR comprise(s) (i) the reverse transcription of RNA (e.g. mRNA) into DNA (e.g. cDNA) using a RNA-dependent DNA polymerase (i.e. a reverse transcriptase), (ii) the amplification of the DNA produced by reverse transcription using PCR, and (iii) the detection and quantification of the amplification products in real time.

Suitable reverse transcriptases are known to the skilled artisan. The following reverse transcriptases are given as examples, but shall in no way limit the scope of the present invention: HIV reverse transcriptase, M-MLV reverse transcriptase, EAIV reverse transeriptase, AMV reverse transcriptase, *Thermos thermophilus* DNA polymerase I, M-MLV RNAse H minus, Superscript, Superscript II, Superscript III, Monstersript (Epicentre), Omniscript reverse transcriptase (Qiagen), Sensiscript reverse transcriptase (Qiagen), ThermoScript (Invitrogen), Thermo-X (Invitrogen), ArrayScript (Ambion), MultiScribe Reverse Transcriptase (Applied Biosystems) or a combination of two or more enzymes thereof.

Other amplification methods than PCR may likewise be applied, these are for example rolling circle amplification (such as in Liu, et al., "Rolling circle DNA synthesis: Small circular oligonucleotides as efficient templates for DNA polymerases," J. Am. Chem. Soc. 118:1587-1594 (1996).), isothermal amplification (such as in Walker, et al., "Strand displacement amplification—an isothermal, in vitro DNA amplification technique," Nucleic Acids Res. 20(7):1691-6 (1992)), ligase chain reaction (such as in Landegren, et al., "A Ligase-Mediated Gene Detection Technique," Science 241: 1077-1080, 1988, or, in Wiedmann, et al., "Ligase Chain Reaction (LCR)—Overview and Applications," PCR Methods and Applications (Cold Spring Harbor Laboratory Press, Cold Spring Harbor Laboratory, NY, 1994) pp. S51-S64.)). Polymerase chain reaction amplification is preferred.

Amplified products produced by PCR may be detected by any of the methods known in the art. In an embodiment of the invention, the amplified products are detected by fluorescence of a compound such as SYBR® Green (Roche), which binds to double-stranded DNA. In a further embodiment of the invention the double stranded nucleic acid-specific dyes is selected from the group consisting of SYBR® Green I, SYBR® Gold, ethidium bromide, propidium bomide, Pico Green, Hoechst 33258, YO-PRO-I and YO-YO-I, SYTO®9, LC Green®, LC Green® Plus+, EvaGreen™. Use of such fluorescent compounds allows the monitoring of the reaction so that conditions may be optimized to control the amplification process.

Furthermore, the detection of the amplification product may be conducted using labelled oligonucleotide primers or probes, e.g. labelled with a fluorescent dye. The dye may be selected from the group consisting of LightCycler-probes (Roche), TaqMan probes (Roche), FRET probes, UPL probes, molecular beacons, Scorpion-primers, Sunrise-primers, LUX-primers or Amplifluor-primers. Oligonucleotide primers and/or probes may by labelled by fluorescent dyes either covalently or non covalently bound to said oligonucleotide primer or probe, e.g. by one or more fluorescent dyes selected from the group of Fluorescein isothiocyanate (FITC), 6-Carboxyfluorescein (FAM), Xanthen, Rhodamine, 6-Carboxy-2',4',7',4,7-hexachlorofluorescein (HEX), 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine 110; coumarines like umbelliferone, benzimides like Hoechst 33258; phenanthridines like Texas Red, ethidiumbromide, acridine dyes, carbazole dyes, phenoxazine dyes, porphyrin dyes, polymethine dyes, cyanine dyes like Cy3, Cy5, Cy7, SYBR® Green (Roche), BODIPY dyes, Quinoline dyes and Alexa dyes, TET, CAL Fluor Gold 540, VIC, CAL Fluor Orange 560, NED, Quasar 570, Oyster 556, CAL Fluor Red 590, ROX, LC red 610, CAL Fluor Red 610, Texas red, LC red 640, CAL Fluor Red 635, LC red 670, Quasar 670, Oyster 645, and LC red 705.

Furthermore, non-fluorescent Quenchers may be used. In a preferred embodiment the non fluorescent Quenchers are selected from the group consisting of Black Hole Quenchers BHQ1, BHQ2, BHQ3, Dabcyl, Dabsyl, DDQ-I, DDQ-II, Eclipse, Iowa Black FQ, Iowa Black RQ QSY7, QSY9, QYS21, and QSY35. Conditions for quantitative PCR or quantitative reverse transcription PCR are known by the skilled artisan, i.e. the skilled artisan knows how to design gene specific oligonucleotide primers and probes, how to choose the number of PCR-cycles as well as suited temperatures, buffer condition and time spans for reverse transcription, denaturing steps, primer annealing steps and elongation steps.

The skilled artisan is also aware of devices and software for amplification, detection, quantification and evaluation, e.g. LightCycler 1.5, LightCycler480 (Roche), Rotor-Gene 3000 (Corbett Research), ABI 7300, ABI 7500, ABI 7900 HT, StepOnePlus (Applied Biosystems), realplex (Eppendorf), Mx3005 (Stratagene), iCycler iQ, MiniOpticon, MyiQ, CFX96, CFX384 (Bio-Rad).

In particular embodiments of the invention the polymerase used for the PCR is a polymerase from a thermophile organism or a thermostable polymerase or is selected from the group consisting of *Thermus thermophiles* (Tth) DNA polymerase, *Thermus acquaticus* (Tag) DNA polymerase, *Thermotoga maritima* (Tma) DNA polymerase, *Thermococcus litoralis* (Tli) DNA polymerase, *Pyrococcus furiosus* (Pfu) DNA polymerase, *Pyrococcus woesei* (Pwo) DNA polymerase, *Pyrococcus kodakaraensis* KOD DNA polymerase, *Thermus filiformis* (Tfi) DNA polymerase, *Sulfolobus solfataricus* Dpo4 DNA polymerase, *Thermus pacificus* (Tpac) DNA polymerase, *Thermus eggertssonii* (Teg) DNA polymerase, *Thermus brockianus* (Thr) and *Thermus flavus* (Tfl) DNA polymerase.

Oligonucleotide primers may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

The length and the sequence of the oligonucleotide primers must be such that they prime the synthesis of the extension products. Preferred primers have a length of from about 15-100, more preferably about 17-50, most preferably about 17-40 bases.

Oligonucleotide primers used in the method according to the present invention are used for the amplification of the cDNA of the respective marker gene or reference gene. In a preferred embodiment the oligonucleotide primers used in the method according to the invention are suited for the amplification of nucleotides having the cDNA sequence of hepsin (SEQ ID NO. 1 and/or SEQ ID NO. 36), TBP (SEQ ID NO. 2), PSA (SEQ ID NO. 3 and/or SEQ ID NO. 37 and/or SEQ ID NO. 38), PCA3 (SEQ ID NO. 4 or SEQ ID NO. 5), EZH2 (SEQ ID NO. 6), TRPM8 (SEQ ID NO. 7), or prostein (SEQ ID NO. 8). The skilled artisan will unambiguously realize that it not necessary to amplify the whole transcripts of the respective genes. For the purpose of the present invention the amplification of parts of said nucleotides may be sufficient. In one embodiment the amplification products have a length of 50 to 400 nucleotides, preferably 100 to 300 nucleotides, most preferred 120 to 282 nucleotides.

In a preferred embodiment of the present invention the expression level of hepsin is determined using oligonucleotide primers having the sequence of SEQ ID NO. 9 and SEQ ID NO. 10, and/or the expression level of TBP is determined using oligonucleotide primers having the sequence of SEQ ID NO. 11 and SEQ ID NO. 12, and/or the expression level of PSA is determined using oligonucleotide primers having the sequence of SEQ ID NO. 13 and SEQ ID NO. 14, and/or the expression level of PCA3 is determined using oligonucleotide primers having the sequence of SEQ ID NO: 15 and SEQ ID NO. 16, and/or the expression level of EZH2 is determined using oligonucleotide primers having the sequence of SEQ ID NO. 17 and SEQ ID NO 18, and/or the expression level of TRPM8 is determined using oligonucleotide primers having the sequence of SEQ ID NO. 19 and SEQ ID NO. 20, and/or the expression level of prostein is determined using oligonucleotide primers having the sequence of SEQ ID NO. 21 and SEQ ID NO. 22.

Preferred oligonucleotide probes used in the method according to the present invention are given in the sequence listing. Thus in a preferred embodiment of the present invention the amplification products of hepsin are detected using oligonucleotide probes having the sequence of SEQ ID NO. 23 and/or using oligonucleotide probes having the sequence of SEQ ID NO. 24, amplification products of TBP are detected using oligonucleotide probes having the sequence of SEQ ID NO. 25 and/or using oligonucleotide probes having the sequence of SEQ ID NO. 26, amplification products of PSA are detected using oligonucleotide probes having the sequence of SEQ ID NO. 27 and/or using oligonucleotide probes having the sequence of SEQ ID NO. 28, amplification products of PCA3 are detected using oligonucleotide probes having the sequence of SEQ ID NO. 29, amplification products of EZH2 are detected using oligonucleotides having the sequence of SEQ ID NO. 30 and/or using oligonucleotide probes having the sequence of SEQ ID NO. 31, amplification products of TRPM8 are detected using oligonucleotides having the sequence of SEQ ID NO. 32 and/or using oligonucleotide probes having the sequence of SEQ ID NO. 33, and amplification products of prostein are detected using oligonucleotides having the sequence of SEQ ID NO. 34 and/or using oligonucleotide probes having the sequence of SEQ ID NO. 35.

The urine samples may be subjected to one or more pretreatments prior to the analysis. Such pre-treatments include, but are not limited to dilution, filtration, centrifugation, concentration, sedimentation, precipitation, dialysis, adsorption, linkage, depletion. Pre-treatments may also include the addition of chemical or biochemical substances to the solution, such as acids, bases, buffers, salts, solvents, reactive dyes, detergents, emulsifiers, chelators, other lysis reagents and stabilizing agents, linkers, adsorbers, ligands, cognitive molecules such as antibodies, aptamers and derivatives thereof.

In a preferred embodiment of the present invention cells contained in the urine sample are harvested by centrifugation prior to the analysis. Thus, the method according to the present invention may comprise the steps of (i) digital-rectal-examination of a subject; (ii) taking a urine sample from said subject directly after said digital-rectal-examination; (iii) harvesting cells from said urine sample; (iv) extracting RNA from the harvested cells; (v) generating cDNA from said RNA by reverse transcription; (vi) determining the expression level of at least hepsin and at least one reference gene by quantitative real-time PCR using gene specific primers and/or probes; (vii) normalizing the expression level of at least hepsin with the determined expression level of said at least one reference gene; and (viii) attributing the presence and/or level of transcripts of hepsin or the transcripts of a set of marker genes according to the present invention to the presence of prostate cancer in said subject and/or an increased risk of said subject acquiring prostate cancer.

The skilled artisan will recognize that the harvested cells can be stored, e.g. by freezing, and the subsequent steps could be conducted later on. Furthermore, in one embodiment of the present invention stabilizing agents and/or buffers are added to the harvested cells. Agents and buffers stabilizing said cells and/or RNA and/or DNA and/or proteins contained therein are commonly known in the art. Non-limiting examples for such stabilizing agents and/or buffers are Lysis Solution R (Invisorb Spin cell RNA Mini Kit; Invitek) and stabilizing agents and/or buffers contained in a kit selected from the group consisting of PrepEase RNA Spin Kit (Affymetrix/USB), Agilent Total RNA Isolation Mini Kit (Agilent Technologies), Total RNA Isolation Spin Kit (AppliChem), illustra RNAspin Mini Kit (GE Healthcare), High Pure RNA isolation kit (Roche Applied Science), GenElute Mammalian Total RNA Miniprep Kit (Sigma-Aldrich), Mini RNA Isolation Kit (Zymo Research), RNeasy Mini Kit (QIAGEN), ArrayPure Nano-scale RNA Purification Kit (Biozym), Total RNA Isolation Kit (Promokine).

In a preferred embodiment of the present invention cells are lysed prior to the RNA extraction from the sample. Methods for lysis of cells are well known in the art and comprise mechanical lysis and/or chemical lysis of cells. Mechanical lysis may be performed using glass, ceramic, zirconium, and/or steel beads combined with a high level of agitation by stirring or shaking, French pressure cell press and/or sonication. Chemical lysis of cells in a method according to the present invention can be reached by addition of different lysing agents and/or buffers. Lysing agents and buffers a well known in the art and comprise detergents (e.g. sodium dodecyl sulfate, Triton, CHAPS), Combinations of mechanical and chemical lysis may be used in the method according to the invention. In one embodiment of the present invention agents and/or buffers are added to stabilize RNA and/or DNA and/or proteins during said lysis.

FIGURE LEGENDS

FIG. 1: Distribution of relative expression levels of hepsin normalized to TBP in patients with (Tu; N=66) and without (Tf; N=62) prostate cancer. The boxes within the plots represent the $25^{th}$-$75^{th}$ percentiles. Medians are depicted as solid lines. White circles and asterisks indicate outlier values.

Figure 2:
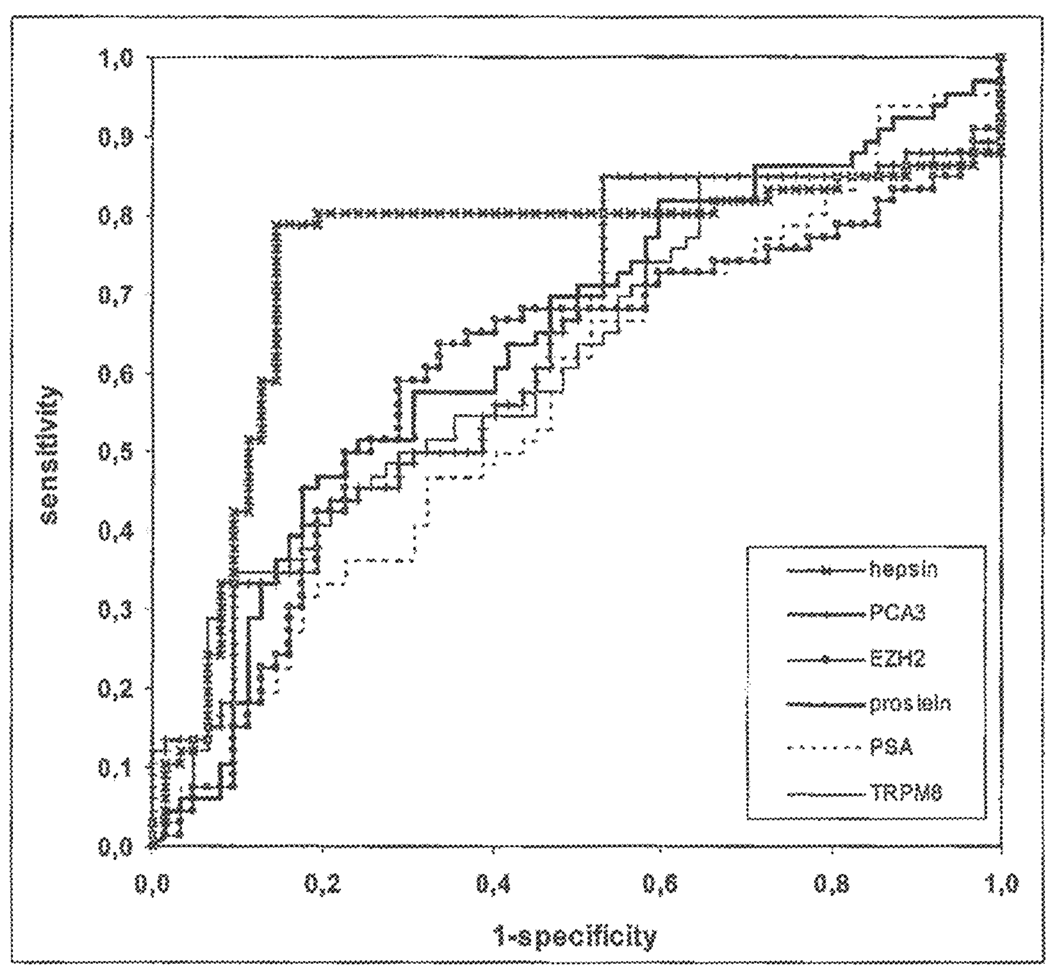

FIG. 2: Receiver Operating Characteristics of the single markers

EXAMPLES

Material and Methods

Study Setting, Inclusion/Exclusion Criteria

The study was set at the Department of Urology of the University Hospital of Dresden, Germany. Urine samples were collected between April 2008 and May 2009. Patients undergoing a radical prostatectomy due to their previously detected prostate cancer served as “tumor” (Tu) group. Patients without histo-pathologically proven prostate cancer after a prostate biopsy or a transurethral resection of the prostate (TUR-P) served as “tumor-free” (Tf) group. Additionally, patients who came for preventive medical checkup were included in the Tf-group if no clinical or laboratory signs of suspicion of having prostate cancer were found.

In total, 128 informative cases (66 patients with prostate cancer and 62 patients without prostate cancer) were included in the analyses so far.

Histo-pathological examination of prostate tissue samples (e.g. radical prostatectomy explants, prostate biopsies or resection specimens) was the decisive determination whether patients were classified as tumor patients. Patients without an informed consent were excluded.

Sample Preparation

Urine samples were taken from 66 patients with an approved prostate cancer and 62 patients without prostate cancer. Before urine sampling patients had undergone DRE for first assessment of suspicion of presence of prostate cancer. Directly after the DRE (about 3 strokes per lobe, from the base to the apex and from the lateral to the median line) up to 100 ml of the first catch urine of the patient have to be collected in a urine collection cup. This urine specimen has to be transferred to a laboratory within 30 minutes.

Cells contained in the urine sample are collected by centrifugation (5 min/860×g/4° C.). After discarding the supernatant, the pelletized cells are resuspended in 1 ml of ice-cold PBS (phosphate buffered saline). The cell suspension is filled up with ice-cold PBS to a final volume of 50 ml and centrifuged again (5 min/860×g/4° C.). This washing step will be repeated with 10 ml of ice-cold PBS.

After complete removal of the supernatant the cell pellet is solubilized in an appropriate volume of a specific lysis solution that additionally serves as stabilizer of the RNA (e.g. Lysis Solution R from the Invisorb Spin cell RNA Mini Kit; Invitek; Berlin). According to the manufacturer’s recommendations total RNA is isolated from the solubilized cell pellet, eluted in water and used for reverse transcription. For this purpose, the 500 ng or—if not available—the total amount of the isolated RNA is brought to a final volume of 10 µl. Superscript II reverse transcriptase (Invitrogen, Karlsruhe, Germany) and random hexamer primers (e.g. from Amersham GE Healthcare, Freiburg, Germany) are used following the manufacturers’ instructions. Resulting cDNA samples can be diluted (1:2 to 1:5, appropriate to the sensitivity of the following measurements) with water and stored at 4° C. or −20° C. until further use.

Quantitative real-time PCR (qPCR) is performed using gene-specific primers and probes (e.g. hydrolyzation/Taqman probes or hybridization/FRET probes or UPL probes from the Roche Universal Probe Library; see Table 5 and 6 respectively) and at least one suitable master mix (containing at least buffer, $Mg^{2+}$, dNTPs and a thermally stable polymerase) on a real-time PCR device (e.g. LightCycler; Roche, Mannheim, Germany). In addition to the selected PCa-specific transcript markers a suitable reference gene is measured by qPCR.

All measurements are performed with aliquots of the same cDNA dilutions within short time periods to ensure standardized and comparable conditions. All qPCR assays are carried out at least twice as independent PCR runs for each cDNA sample. Samples are measured for a third time if differences of >30% occurred. The means of all repeat measurements are used for further calculations.

The copy numbers of the single transcript markers are calculated in relation to the amplification product amounts of corresponding external standards. Quantity standard curves are generated for each transcript marker employing reaction vessels storage-stable coated with amounts of $10^1$ to $10^7$ molecules of HPLC-calibrated PCR fragments. Relative expression levels of the PCa-related markers are obtained by normalization to the reference gene (transcripts of the marker per transcripts of the reference gene). The results are given in Table 1. These relative expression levels of the PCa-specific markers serve as operand for univariate and multivariate analyses. Serum PSA levels was measured as a reference on a AxSym device from Abbott Diagnostics GmbH & Co. KG (Wiesbaden, Germany).

Data Analysis

TABLE 1

Baseline data

| PAT. NO. | sample-Nr. | Age | serum PSA ng/ml | PCa 1 = yes; 0 = no | PCA3/TBP. | EZH2/TBP. | TRPM8/TBP. | prostein/TBP. | PSA/TBP. | hepsin/TBP. |
|---|---|---|---|---|---|---|---|---|---|---|
| 1 | PU 002 | 68 | 7.29 | 1 | 0.86 | 0.99 | 0.01 | 0.1 | 1.02 | 0.03 |
| 2 | PU 005 | 72 | 4 | 1 | 0.11 | 0 | 0 | 11.83 | 0.05 | 0.13 |
| 3 | PU 006 | 72 | 5.18 | 1 | 0 | 1.08 | 0 | 0.39 | 0.42 | 0 |
| 4 | PU 007 | 62 | 6.52 | 1 | 0.24 | 1.87 | 0.15 | 0.09 | 0.82 | 0.02 |
| 5 | PU 008 | 53 | 10.85 | 1 | 0.28 | 1.45 | 0.4 | 0.61 | 7.89 | 0.06 |
| 6 | PU 009 | 55 | 8.49 | 1 | 4.78 | 2.26 | 1.07 | 1.22 | 16.91 | 0.44 |
| 7 | PU 010 | 58 | 3.43 | 1 | 1.36 | 1.37 | 0.64 | 0.98 | 5.17 | 0.07 |
| 8 | PU 011 | 70 | 1.66 | 1 | 0 | 1.17 | 0.45 | 0.54 | 1.41 | 0 |
| 9 | PU 012 | 48 | 4.2 | 1 | 0.13 | 1.39 | 0.09 | 0.52 | 2.85 | 0.1 |
| 10 | PU 013 | 59 | 4.03 | 1 | 0 | 1.01 | 0 | 0.61 | 0.38 | 0.03 |
| 11 | PU 014 | 66 | 2.61 | 1 | 3.51 | 0.89 | 4.83 | 0.27 | 16.11 | 0.11 |
| 12 | PU 015 | 63 | 19.81 | 1 | 0.08 | 1.59 | 0.24 | 0.21 | 0.2 | 0.19 |
| 13 | PU 016 | 58 | 9.55 | 1 | 1.84 | 1.32 | 0.66 | 0.12 | 4.93 | 0.08 |
| 14 | PU 017 | 74 | 8.05 | 1 | 0.77 | 3.16 | 0.36 | 0.53 | 2.85 | 0.26 |
| 15 | PU 018 | 46 | 7.31 | 1 | 0.04 | 3.9 | 0.02 | 0.18 | 0.35 | 0.23 |
| 16 | PU 019 | 67 | 8.64 | 1 | 0.37 | 1.06 | 11.69 | 6.48 | 208.17 | 3.5 |
| 17 | PU 021 | 57 | 7.81 | 1 | 0 | 1.85 | 0.16 | 0.12 | 1.18 | 0.15 |
| 18 | PU 022 | 64 | 4.36 | 1 | 1.46 | 1.57 | 2.85 | 2.58 | 19.88 | 0 |
| 19 | PU 023 | 65 | 4.42 | 1 | 0 | 1.35 | 0 | 0.17 | 0.72 | 0.1 |
| 20 | PU 024 | 67 | 2.21 | 1 | 0.03 | 1.84 | 0 | 0.06 | 0 | 0.05 |
| 21 | PU 025 | 60 | 7.18 | 1 | 0.05 | 1.15 | 0.04 | 0.08 | 0.08 | 0.02 |
| 22 | PU 026 | 74 | 5.46 | 1 | 0.49 | 1.48 | 2.21 | 0.84 | 11.74 | 0.07 |
| 23 | PU 027 | 68 | 15.27 | 1 | 0.01 | 4.28 | 0.01 | 0.04 | 0.03 | 0.07 |
| 24 | PU 028 | 64 | 5.54 | 1 | 0.03 | 1.69 | 0.17 | 0.12 | 0.54 | 0.22 |
| 25 | PU 029 | 67 | 5.15 | 1 | 0.03 | 2.1 | 0.09 | 0.09 | 0.24 | 0.04 |
| 26 | PU 030 | 52 | 6.29 | 1 | 0.01 | 1.7 | 0.14 | 0.04 | 0.29 | 0.08 |
| 27 | PU 031 | 56 | 15.63 | 1 | 0.4 | 4.62 | 1.17 | 0.11 | 4.98 | 0.15 |
| 28 | PU 032 | 73 | 12.55 | 1 | 7.14 | 2.97 | 5.88 | 0.9 | 49.43 | 0.5 |
| 29 | PU 033 | 73 | 1.47 | 1 | 0.56 | 1.95 | 0.19 | 0.14 | 37.18 | 0.08 |
| 30 | PU 034 | 55 | 8.61 | 1 | 0.1 | 1.21 | 0.47 | 0.2 | 2.21 | 0.03 |
| 31 | PU 035 | 73 | 8.31 | 1 | 2.22 | 2.62 | 0.96 | 0.19 | 2.55 | 0.11 |
| 32 | PU 036 | 71 | 27.65 | 1 | 0.83 | 2.54 | 0.65 | 0.37 | 7.26 | 0.86 |
| 33 | PU 037 | 53 | 5.02 | 1 | 0.17 | 3.42 | 0.2 | 0.27 | 2.46 | 0.06 |
| 34 | PU 038 | 66 | 4.71 | 1 | 0.42 | 3.55 | 0.13 | 0.13 | 1.23 | 0.55 |
| 35 | PU 039 | 69 | 7.26 | 1 | 0.03 | 1.29 | 0.03 | 0.08 | 0.1 | 0.07 |
| 36 | PU 040 | 66 | 24.81 | 1 | 9.29 | 6.59 | 1.43 | 32.48 | 32.33 | 2.5 |
| 37 | PU 041 | 55 | 18.26 | 1 | 1.06 | 2.31 | 1.74 | 0.19 | 6.42 | 0.98 |
| 38 | PU 042 | 67 | 6.97 | 1 | 0.14 | 1.29 | 0.19 | 0.72 | 0.51 | 0 |
| 39 | PU 043 | 66 | 7.26 | 1 | 0.06 | 1.67 | 0.04 | 0.13 | 0.17 | 0.03 |
| 40 | PU 044 | 61 | 17.89 | 1 | 0.02 | 2.38 | 0.01 | 0.14 | 0.06 | 0.16 |
| 41 | PU 045 | 56 | 9.6 | 1 | 0.04 | 2.08 | 0.13 | 0.12 | 0.9 | 0.31 |
| 42 | PU 046 | 69 | 4.78 | 1 | 0.16 | 0.75 | 0.58 | 0.35 | 2.3 | 0.2 |
| 43 | PU 047 | 73 | 9.84 | 1 | 0.48 | 0.57 | 0.48 | 0.21 | 1.26 | 0.05 |
| 44 | PU 048 | 61 | 5.82 | 1 | 1.1 | 1.83 | 0.46 | 0.35 | 3.73 | 0 |
| 45 | PU 049 | 70 | 6.94 | 1 | 2.97 | 3.02 | 1.13 | 0.65 | 9.49 | 0 |
| 46 | PU 050 | 63 | 9.66 | 1 | 1.23 | 5.43 | 1.68 | 0.8 | 5.03 | 0.04 |
| 47 | PU 051 | 71 | 6.84 | 1 | 0.33 | 14.81 | 0 | 2.34 | 1.02 | 0 |
| 48 | PU 052 | 58 | 10.83 | 1 | 1.21 | 18.11 | 1.03 | 0.56 | 3.11 | 0.11 |
| 49 | PU 053 | 60 | 4.82 | 1 | 0 | 16.08 | 4.8 | 0.93 | 6.54 | 0.15 |
| 50 | PU 054 | 68 | 6.73 | 1 | 1.31 | 8.04 | 2.11 | 1.8 | 20.93 | 0.1 |
| 51 | PU 055 | 66 | 6.48 | 1 | 1.02 | 9.62 | 0.33 | 1.2 | 0.52 | 0.2 |
| 52 | PU 056 | 66 | 6.71 | 1 | 0.04 | 0.39 | 0.01 | 0.53 | 0 | 0.02 |
| 53 | PU 057 | 66 | 4.99 | 1 | 0.25 | 8.61 | 0.34 | 0.82 | 1.45 | 0.06 |
| 54 | PU 058 | 65 | 4.67 | 1 | 0.05 | 4.79 | 0.09 | 0.29 | 1.15 | 0.01 |
| 55 | PU 059 | 71 | 12.57 | 1 | 2.79 | 13.46 | 1.35 | 2.18 | 49.31 | 0.14 |
| 56 | PU 060 | 54 | 3.92 | 1 | 0 | 10.52 | 0 | 0 | 3.07 | 0 |
| 57 | PU 061 | 63 | 9.08 | 1 | 5.59 | 11.79 | 0.27 | 30.48 | 0.72 | 0.19 |
| 58 | PU 062 | 63 | 17.29 | 0 | 0 | 1.45 | 0.05 | 0.19 | 0.65 | 0 |
| 59 | PU 063 | 71 | 16.51 | 0 | 0 | 2.64 | 0 | 0 | 0 | 0 |
| 60 | PU 064 | 71 | 46.09 | 1 | 0 | 2.43 | 0 | 0 | 0 | 0 |
| 61 | PU 065 | 57 | 5.81 | 0 | 0.05 | 3.47 | 0.03 | 0.13 | 0.41 | 0.01 |
| 62 | PU 066 | 64 | 2.69 | 1 | 0.07 | 1.49 | 0.05 | 0.13 | 0.52 | 0.03 |
| 63 | PU 067 | 72 | 7.09 | 0 | 0.04 | 0.01 | 0.09 | 0.1 | 1.18 | 0 |
| 64 | PU 068 | 79 | 1.41 | 0 | 0 | 5.59 | 0.5 | 0.22 | 0.49 | 0 |
| 65 | PU 069 | 78 | 3.28 | 0 | 0 | 3.79 | 0.18 | 0.16 | 0 | 0 |
| 66 | PU 071 | 73 | 2.8 | 0 | 2.23 | 4.44 | 0 | 1 | 3.04 | 0 |
| 67 | PU 072 | 72 | 0.97 | 0 | 0.37 | 2.29 | 4.97 | 0.75 | 6.8 | 0 |
| 68* | PU 073* | 67 | 0.32 | 1 | 1.56 | 1.68 | 2.5 | 0 | 6.03 | 0 |
| 69 | PU 074 | 76 | 1.88 | 0 | 0.48 | 4.01 | 0 | 0 | 0.48 | 0 |

TABLE 1-continued

| Baseline data | | | | | | | | | | |
|---|---|---|---|---|---|---|---|---|---|---|
| PAT. NO. | sample-Nr. | Age | serum PSA ng/ml | PCa 1 = yes; 0 = no | PCA3/TBP. | EZH2/TBP. | TRPM8/TBP. | prostein/TBP. | PSA/TBP. | hepsin/TBP. |
| 70 | PU 075 | 71 | 0.64 | 0 | 0 | 2.71 | 0 | 0.08 | 0 | 0 |
| 71 | PU 076 | 67 | 8.04 | 0 | 0.29 | 2.73 | 0.2 | 0.29 | 0.68 | 0 |
| 72 | PU 078 | 72 | 1.14 | 0 | 0 | 3.5 | 0.2 | 0.23 | 0 | 0 |
| 73 | PU 079 | 73 | 2.11 | 0 | 0 | 2.96 | 0 | 0.3 | 0.21 | 0 |
| 74 | PU 081 | 70 | 3.97 | 1 | 0 | 7.58 | 0 | 0 | 1.08 | 0 |
| 75 | PU 083 | 71 | 0.98 | 0 | 0.11 | 1.17 | 0.15 | 0.75 | 0.31 | 0 |
| 76 | PU 084 | 73 | 0.77 | 0 | 0.11 | 2.46 | 0.13 | 0.99 | 0.43 | 0.1 |
| 77 | PU 085 | 80 | 2.51 | 0 | 0.18 | 2.03 | 0.02 | 0.54 | 0.07 | 0.02 |
| 78 | PU 086 | 75 | 3.88 | 0 | 0.35 | 1.88 | 0.18 | 1.01 | 1.43 | 0 |
| 79 | PU 087 | 67 | 2.62 | 0 | 0 | 1.57 | 0 | 0.39 | 0.11 | 0 |
| 80 | PU 088 | 74 | 2.53 | 0 | 1.36 | 1.75 | 0 | 1.64 | 2.85 | 0 |
| 81 | PU 089 | 67 | 1.35 | 0 | 0 | 0.75 | 0 | 0.42 | 0 | 0 |
| 82 | PU 090 | 72 | 6.84 | 1 | 0 | 0.48 | 0 | 0.88 | 0 | 0 |
| 83 | PU 091 | 58 | 2.16 | 0 | 0.13 | 0.49 | 0.16 | 0.55 | 0.66 | 0 |
| 84 | PU 092 | 78 | 1.47 | 0 | 0.06 | 2.39 | 0.03 | 0.23 | 0 | 0 |
| 85 | PU 093 | 70 | 0.39 | 0 | 0 | 1.11 | 0 | 0.41 | 0 | 0 |
| 86 | PU 094 | 64 | 2.17 | 0 | 0 | 0.84 | 0.08 | 0.57 | 0.08 | 0 |
| 87* | PU 095* | 71 | 3.1 | 1 | 0.47 | 1.84 | 1.31 | 1.26 | 2.68 | 0 |
| 88* | PU 096* | 67 | 10.44 | 1 | 3.7 | 2.36 | 1.53 | 4.91 | 5.18 | 0.19 |
| 89 | PU 097 | 71 | 16.64 | 0 | 1.88 | 0.88 | 0.41 | 1.45 | 3.41 | 0 |
| 90 | PU 098 | 70 | 11.29 | 1 | 0.09 | 2.07 | 0.02 | 0.19 | 0.02 | 0.02 |
| 91 | PU 099 | 70 | 1.69 | 0 | 0.22 | 3.42 | 0.48 | 1.13 | 0.26 | 0.13 |
| 92 | PU 100 | 66 | 2.11 | 0 | 0.25 | 2.05 | 0.29 | 1.11 | 2.86 | 0 |
| 93 | PU 101 | 65 | 1.63 | 0 | 0.51 | 1.31 | 0.17 | 1.03 | 1.66 | 0 |
| 94 | PU 102 | 71 | 1.59 | 0 | 0.36 | 2.31 | 0 | 1.34 | 1.38 | 0 |
| 95 | PU 103 | 66 | 4.21 | 0 | 0 | 0.38 | 0 | 0 | 0 | 0 |
| 96 | PU 105 | 62 | 15.03 | 1 | 0.08 | 2.18 | 0.09 | 0.23 | 0.1 | 0.08 |
| 97 | PU 107 | 69 | 1.02 | 0 | 0.58 | 3.35 | 0.34 | 0.5 | 3.62 | 0 |
| 98 | PU 108 | 72 | 1.44 | 0 | 0 | 3.1 | 0 | 0.3 | 0 | 0 |
| 99 | PU 109 | 57 | 2.3 | 0 | 0 | 1.91 | 0 | 0.8 | 2.14 | 0 |
| 100 | PU 110 | 73 | 2.27 | 0 | 0.09 | 2.59 | 0.11 | 0.33 | 0.43 | 0.02 |
| 101 | PU 112 | 76 | 1.97 | 0 | 0 | 4.44 | 0 | 0.83 | 14.32 | 0 |
| 102 | PU 113 | 72 | 3.38 | 0 | 1.85 | 7.39 | 0 | 11.16 | 0.47 | 0.05 |
| 103 | PU 114 | 47 | 0.7 | 0 | 0 | 1.77 | 0 | 0.53 | 0.26 | 0.07 |
| 104 | PU 115 | 64 | 2.17 | 0 | 0.19 | 2.5 | 0.1 | 0.41 | 0.86 | 0.01 |
| 105 | PU 116 | 66 | 1.47 | 0 | 0.06 | 3.38 | 0.02 | 1.81 | 0.15 | 0.01 |
| 106 | PU 118 | 69 | 1.96 | 0 | 0.32 | 3.53 | 0.92 | 0.71 | 8.48 | 0 |
| 107 | PU 119 | 61 | | 0 | 0.58 | 2.95 | 1.99 | 2.94 | 39.6 | 0 |
| 108 | PU 120 | 59 | 5.51 | 0 | 0.2 | 3.57 | 0.53 | 0.89 | 7.66 | 0 |
| 109 | PU 121 | 57 | 1.3 | 0 | 0 | 2.69 | 0.51 | 0 | 1.86 | 0 |
| 110 | PU 122 | 59 | 3.55 | 0 | 0 | 2.58 | 0.58 | 1.11 | 5.11 | 0 |
| 111 | PU 123 | 74 | 1.95 | 0 | 0 | 9.75 | 0 | 0.18 | 0.48 | 0.19 |
| 112 | PU 124 | 62 | 34.49 | 0 | 0 | 5.73 | 0 | 0.3 | 0.33 | 0 |
| 113 | PU 125 | 78 | 2.11 | 0 | 0 | 5.5 | 0 | 0 | 2.98 | 0 |
| 114 | PU 126 | 73 | 0.55 | 0 | 1.74 | 4.85 | 5.75 | 16.4 | 91.84 | 0.36 |
| 115 | PU 127 | 75 | 1.15 | 0 | 0.31 | 6.65 | 0.51 | 2.29 | 7.35 | 0.28 |
| 116 | PU 128 | 67 | 0.32 | 0 | 0 | 4.24 | 0.22 | 1.51 | 3.81 | 0 |
| 117 | PU 129 | 74 | 0.45 | 0 | 0 | 2.83 | 0.2 | 0.4 | 0.88 | 0 |
| 118 | PU 130 | 68 | 2.39 | 0 | 0 | 2.38 | 0 | 0.66 | 1.23 | 0 |
| 119 | PU 131 | 74 | 1.78 | 0 | 0.65 | 1.34 | 0.17 | 3.28 | 3.02 | 0 |
| 120 | PU 132 | 63 | 0.72 | 0 | 0 | 2.34 | 0 | 2.51 | 6.91 | 0 |
| 121 | PU 133 | 76 | 2.04 | 0 | 0.2 | 3.81 | 0.33 | 0.74 | 1.07 | 0.24 |
| 122 | PU 134 | 69 | 0.99 | 0 | 0.53 | 4.59 | 0.17 | 1.62 | 2.63 | 0 |
| 123 | PU 135 | 59 | 0.78 | 0 | 0 | 3.19 | 0.26 | 1.32 | 0.59 | 0 |
| 124 | PU 136 | 50 | 0.54 | 0 | 0.12 | 9.92 | 0.44 | 1.56 | 6.32 | 0 |
| 125 | PU 137 | 72 | 2.14 | 0 | 2.15 | 2.73 | 3.56 | 5.95 | 28.38 | 0 |
| 126 | PU 138 | 76 | 0.96 | 0 | 0 | 2.86 | 0.35 | 2.63 | 0.42 | 1.34 |
| 127 | PU 139 | 73 | 1.05 | 0 | 0 | 8.61 | 0 | 10.47 | 1.74 | 0 |
| 128 | PU 140 | 80 | 2.78 | 0 | 0 | 3.44 | 0.17 | 14.94 | 1.33 | 0 |

*Patient with confirmed AAH

Example 1

Comparison of the Relative Expression Levels (Average and Median) Between Patients with (Tu) and without (Ti) Prostate Cancer (as Tu/Tf Ratios)

For each prostate-associated transcript marker (normalized to the reference gene TBP) the values for the averages, medians and standard deviations (SD) as well as the bounds of evidence in the tumor (Tu) group and the tumor-free (Tf) group are given. To reflect the degree of up- or down-regulation of the respective marker in the Tu group, the ratios of the relative expression levels in the urine samples form prostate cancer patients and from patients without evidence of prostate cancer were calculated by division of the average or median levels per group. The Mann-Whitney U-test was used for statistical calculation whether expression levels of the markers are significantly different between the Tu group and the Tf group. Resulted values equal zero are substituted by a value at the bound of evidence.

TABLE 2

Comparison of the relative expression levels (average and median) between patients with (Tu) and without (Tf) prostate cancer (as Tu/Tf ratios)

| | | PCA3/TBP | EZH2/TBP | TRPM8/TBP | prostein/TBP | PSA/TBP | hepsin/TBP |
|---|---|---|---|---|---|---|---|
| average | Tu | 0.96 | 3.54 | 0.90 | 1.76 | 8.75 | 0.21 |
| | Tf | 0.30 | 3.18 | 0.41 | 1.71 | 4.45 | 0.05 |
| median | Tu | 0.20 | 1.91 | 0.22 | 0.28 | 1.34 | 0.07 |
| | Tf | 0.05 | 2.73 | 0.12 | 0.73 | 0.87 | 0.00 |
| SD | Tu | 1.75 | 3.97 | 1.80 | 5.57 | 27.08 | 0.54 |
| | Tf | 0.55 | 2.05 | 1.05 | 3.27 | 12.96 | 0.18 |
| bound of evidence | | 0.001 | 0.01 | 0.001 | 0.01 | 0.01 | 0.001 |
| average Tu/ average Tf | | 3.21 | 1.12 | 2.19 | 1.03 | 1.97 | 4.60 |
| median Tu/ median Tf | | 4.01 | 0.70 | 1.78 | 0.39 | 1.53 | 71.9 |
| p value Mann-Whitney U test | | 0.0015 | 0.0636 | 0.0082 | 0.0082 | 0.1398 | <.0001 |

$N_{Tu} = 66$, $N_{Tf} = 62$

An obvious up-regulation of the respective transcript marker (normalized to the reference gene TBP) in the urine samples originating from prostate cancer patients was found for PCA3, TRPM8, PSA and particularly for hepsin.

Example 2

Thresholds for the Relative Expression Levels of Different Marker Genes Normalized to TBP and Predictive Values for Exemplified Pre-Test Probabilities, Likelihood Ratios and AUC Values Table 3 gives the regression coefficients and their statistical characteristics for the logistic model which predicts the probability of tumor, and an example for the calculation for an exemplary patient.

TABLE 3

Final logistic regression model using four genes, and computation of certainty of diagnosis for a exemplary patient

| Variable | Regression coefficient | standard error | p-value | exemplary value of a patient | contribution to the logit of the patient |
|---|---|---|---|---|---|
| Intercept | 2.8279 | 2.1906 | 0.1967 | | 2.8279 |
| $(PCA\ 3/TBP)^{1/3}$ | 3.0726 | 0.8711 | 0.0004 | 0.245 | $3.0726 * 0.245^{1/3} = 1.9226$ |
| $(EZH2/TBP)^{1/2}$ | −3.7418 | 1.0856 | 0.0006 | 2.047 | $-3.7418 * 2.047^{1/2} = -5.3535$ |
| $(EZH2/TBP)^3 * 10^{-3}$ | 7.3317 | 2.4166 | 0.0024 | | $7.3317 * 2.047^3 * 10^{-3} = 0.0629$ |
| $(EZH2/TBP)^{-1/3}$ | −1.1307 | 0.5849 | 0.0532 | | $-1.1307 * 2.047^{-1/3} = -0.8905$ |
| $(prostein/TBP)^{-1/3}$ | 2.2638 | 0.7026 | 0.0013 | 1.108 | $2.2638 * 1.108^{-1/3} = 2.1877$ |
| $(prostein/TBP)^{-1/2} * 10^{-6}$ | −512.5 | 249.8 | 0.0402 | | $-512.5 * 1.108^{-1/2} * 10^{-6} = -0.0005$ |
| $(hepsin/TBP)^{-1/2} * 10^{-6}$ | −2.9431 | 0.6391 | <.0001 | 0.001 | $-2.9431 * 0.001^{-1/2}\ 10^{-6} = -2.9431$ |
| | sum of logits | | | | −2.1865 |

Resulting certainty of diagnosis "tumor" for the exemplary patient = exp(−2.1865)/[1 + exp(−2.1865)] = 0.101 = 10.2%

Example 3

Thresholds for the Relative Expression Levels of Different Marker Genes Normalized to TBP and Predictive Values for Exemplified Pre-Test Probabilities, Likelihood Ratios and AUC Values The given thresholds in Table 4 are selected for maximal $LR_+$ in the data of the diagnostic study. The positive predictive values (ppv) gives the certainty of diagnosis "tumor" in the ease of test positive result, and the negative predictive value (npv) gives the certainty of diagnosis "no tumor" in the case of test negative result for 3 different pretest values corresponding to 3 different case mixes in the clinical situation. $LR_+$ is the factor for the increase of the pretest odds for the diagnosis "tumor" in the case of a test positive result, and $LR_-$ is the inverse of the factor for the increase of the pretest odds for the diagnosis "no tumor" in the case of a test negative result. The AUC of the ROC estimates the rate of right diagnoses independently of the threshold for the test positive measure range. The 95% confidence interval for the AUC is an information on the precision of the estimation. AUC and their confidence interval are computed following DeLong R, DeLong D, Clarke-Pearson D: Comparing the Areas Under Two or More Correlated Receiver Operating Characteristic Curves: A Nonparametric Approach. Biometrics 44 (1988) 837-845.

All characteristics result from the analysis of the distributions of the markers in the data of the diagnostic study.

$$ppW = \frac{\text{Sensitivity} \cdot Pretestvalue}{\text{Sensitivity} \cdot Pretestvalue + (1 - Spezificity) \cdot (1 - Pretestvalue)}$$

$$npW = \frac{Spezificity \cdot Pretestvalue}{Spezificity \cdot Pretestvalue + (1 - \text{Sensitivity}) \cdot (1 - Pretestvalue)}$$

$$LR_{+} = \frac{\text{Sensitivity}}{1 - Spezificity}$$

$$LR_{-} = \frac{1 - Sensitifity}{1 - Specificity}$$

$$PosttestOdds_{+} = LR_{+} \cdot PretestOdds_{+}$$

$$PosttestOdds_{-} = 1 / LR_{-} \cdot PretestOdds_{-}$$

TABLE 4

Thresholds for the relative expression levels of different marker genes normalized to TBP and predictive values for exemplified pre-test probabilities, likelihood ratios and AUC values.

| Marker gene/ reference gene | Threshold for test positive result | Pretest probability | ppv | npv | $LR_{+}$ | $LR_{-}$ | AUC | 95% CI for AUC |
|---|---|---|---|---|---|---|---|---|
| PCA3/TBP | ≥2.15 | 0.30 | 0.78 | 0.33 | 8.45 | 0.88 | 0.661 | 0.4824-0.8387 |
| | | 0.40 | 0.85 | 0.43 | | | | |
| | | 0.50 | 0.89 | 0.53 | | | | |
| EZH2/TBP | ≤1.87 | 0.30 | 0.49 | 0.40 | 2.21 | 0.65 | 0.596 | 0.4236-0.7685 |
| | | 0.40 | 0.60 | 0.51 | | | | |
| | | 0.50 | 0.69 | 0.61 | | | | |
| TRPM8/TBP | ≥0.58 | 0.30 | 0.64 | 0.37 | 4.13 | 0.72 | 0.637 | 0.461-0.8118 |
| | | 0.40 | 0.73 | 0.48 | | | | |
| | | 0.50 | 0.81 | 0.58 | | | | |
| prostein/TBP | ≤0.21 | 0.30 | 0.52 | 0.39 | 2.56 | 0.66 | 0.638 | 0.4625-0.8131 |
| | | 0.40 | 0.63 | 0.50 | | | | |
| | | 0.50 | 0.72 | 0.60 | | | | |
| PSA/TBP | ≥14.32 | 0.30 | 0.55 | 0.32 | 2.82 | 0.91 | 0.576 | 0.4141-0.7384 |
| | | 0.40 | 0.65 | 0.42 | | | | |
| | | 0.50 | 0.74 | 0.52 | | | | |
| hepsin/TBP | ≥0.0168 | 0.30 | 0.70 | 0.63 | 5.43 | 0.25 | 0.802 | 0.5943-1.0103 |
| | | 0.40 | 0.78 | 0.71 | | | | |
| | | 0.50 | 0.84 | 0.80 | | | | |

ppv: positive predictive value
npv: negative predictive value
$LR_{+}$: positive likelihood ratio
$LR_{-}$: negative likelihood ratio

CONCLUSIONS

The quantification of prostate cancer-associated marker genes in urine samples of patients with a suspected prostate cancer allows the diagnosis of prostate cancer. Within the analyzed marker genes the presence of hepsin transcripts showed the most significant correlation with the presence of prostate cancer. This is absolutely unexpected, as previous study revealed that hepsin could not be detected in blood samples of patients suffering from prostate cancer.

Furthermore, the 4-gene model comprising hepsin, EZH2, prostein and PCA3 provides a reliable marker set for the diagnosis of prostate cancer.

The results of this study showed that prostate cancer cells containing the gene products of the marker genes can be transferred to the bladder/urine by DRE. These findings allowed the development of a non-invasive method for the diagnosis of prostate cancer according to the present application.

TABLE 5

Oligonucleotide primers used

| Name | Sequence (5' to 3') | Amplified gene | Product length | SEQ ID NO. |
|---|---|---|---|---|
| HPN for | CCCCAACAGCGAGGAGAAC | hepsin | 282 bp | 9 |
| HPN rev | GGGTAGCCAGCACAGAACATC | hepsin | | 10 |
| TBP for | GAATATAATCCCAAGCGGTTTG | TBP | 226 bp | 11 |
| TBP rev | ACTTCACATCACAGCTCCCC | TBP | | 12 |
| PSA for | TGCCCACTGCATCAGGAACA | PSA | 158 bp | 13 |
| PSA rev | CATCACCTGGCCTGAGGAATC | PSA | | 14 |
| PCA3 for | TGTTTTTGCACATTTCCAGC | PCA3 | 120 bp | 15 |
| PCA3 rev | GGGCGAGGCTCATCGAT | PCA3 | | 16 |

TABLE 5-continued

Oligonucleotide primers used

| Name | Sequence (5' to 3') | Amplified gene | Product length | SEQ ID NO. |
|---|---|---|---|---|
| EZH2 for | GCCAGACTGGGAAGAAATCTG | EZH2 | 277 bp | 17 |
| EZH2 rev | TGTGTTGGAAAATCCAAGTCA | EZH2 | | 18 |
| TRPM8 for | ACGCTTGTGTACCGGAATCT | TRPM8 | 167 bp | 19 |
| TRPM8 rev | CGAGTAATAGGAGACACGTCG | TRPM8 | | 20 |
| Pro for | GCCAGGATCTGAGTGATGAGA | prostein | 204 bp | 21 |
| Pro rev | GTTCAGGCACTCCAGAACTG | prostein | | 22 |

TABLE 6

| Name | Sequence (5' to 3') | Detected amplification product | SEQ ID NO. |
|---|---|---|---|
| Oligonucleotide probes used | | | |
| HPN FL | GAGTCCCCATAATCAGCAATGATGTCTGCA-FL | hepsin | 23 |
| HPN LC | LCRed640-TGGCGCTGACTTCTATGGAAACCAGATCAA-PH | hepsin | 24 |
| TBP FL | TTTCCCAGAACTGAAAATCAGTGCC-FL | TBP | 25 |
| TBP LC | LCRed640-TGGTTCGTGGCTCTCTTATCCTCATG-PH | TBP | 26 |
| PSA FL | ATTTCAGGTCAGCCACAGCTTCCC-FL | PSA | 27 |
| PSA LC | LCRed640-CACCCGCTCTACGATATGAGCCTCC-PH | PSA | 28 |
| PCA3 Taq | 6FAM-AGAAATGCCCGGCCGCCATC-XT-PH | PCA3 | 29 |
| EZH2 FL | AACCTCTTGAGCTGTCTCAGTCGCA-FL | EZH2 | 30 |
| EZH2 LC | LCRed640-TACTCTGATTTTACACGCTTCCGCC-PH | EZH2 | 31 |
| TRPM8 FL | TTTCCAGACAAACGTGAGGAGGGC-FL | TRPM8 | 32 |
| TRPM8 LC | LCRed640-CATTATAGGAATTCTTGGCGATCTGCA-PH | TRPM8 | 33 |
| Pro FL | CGGTCCAGCTTCTCAGCCCA-FL | prostein | 34 |
| Pro LC | LCRed640-GCTCAACACCTGCTGCTGTGGG-PH | prostein | 35 |

FL: 6-carboxy-fluorescein
PH: phosphorylated 3'-end
XT: 6-carboxytetramethylrhodamin

The invention claimed is:

1. A noninvasive method for diagnosing prostate cancer and/or assessing the risk of a subject acquiring prostate cancer comprising the analysis of the expression of hepsin in an urine sample, wherein the analysis comprises the following steps:

(i) determining the expression level of hepsin in said urine sample;

(ii) determining the expression level of at least one reference gene in said urine sample;

(iii) normalizing the expression level of hepsin to the expression level of the at least one reference gene, and (iv) attributing the normalized expression level of hepsin to the diagnosis of prostate cancer in said subject and/or an increased risk of said subject acquiring prostate cancer, wherein at least one reference gene is TATA-Box binding protein (TBP), wherein optionally in addition to the expression of hepsin the expression of the marker genes PCA3, EZH2 and prostein are analyzed, wherein the expression levels of hepsin, said marker gene(s) and of said at least one reference gene are determined via the quantification of the respective transcripts, and wherein the expression levels of hepsin and said marker genes are normalized by the use of TBP as said at least one reference gene, and wherein a normalized expression level of more than 0.0168 for hepsin and/or a normalized expression level of less than 0.21 for prostein and/or a normalized expression level of less than 1.87 for EZH2 and/or a normalized expression level of more than 2.15 for PCA3 is attributed to an increased likelihood for the presence of prostate cancer in said patient and/or an increased risk of said subject for acquiring prostate cancer.

2. The method according to claim 1, wherein the quantification of said transcripts is conducted by quantitative reverse transcription real-time PCR (q-RT PCR).

3. The method according to claim 1, wherein the expression levels of pepsin is determined using oligonucleotide primers having the sequence of SEQ ID NO. 9 and SEQ ID NO. 10 and/or using oligonucleotide probes having the sequence of SEQ ID NO. 23 and/or using oligonucleotide probes having the sequence of SEQ ID NO. 24, and optionally the expression level of TBP is determined using oligonucleotide probes having the sequence of SEQ ID NO. 11 and SEQ ID NO. 12 and/or using oligonucleotide probes having the sequence of SEQ ID NO. 25 and/or using oligonucleotide probes having the sequence of SEQ ID NO. 26, and/or the expression level of PCA3 is determined using oligonucleotide probes having the sequence of SEQ ID NO: 15 and SEQ ID NO. 16 and/or using oligonucleotide probes having the sequence of SEQ ID NO. 29, and/or the expression level of EZH2 is determined using oligonucleotide primers having the sequence of SEQ ID NO. 17 and SEQ ID NO 18 and/or using oligonucleotide probes having the sequence of SEQ ID NO. 30 and/or using oligonucleotide probes having the sequence of SEQ ID NO. 31, and/or the expression level of prostein is determined using oligonucleotides having the sequence of SEQ ID NO. 21 and SEQ ID NO. 22 and/or using oligonucleotide probes having the sequence of SEQ ID NO. 34 and/or using oligonucleotide probes having the sequence of SEQ ID NO. 35.

4. A method according to claim 2, comprising the following steps:

(i) digital-rectal-examination of a subject;

(ii) taking a urine sample from said subject directly after step (i);

(iii) harvesting cells from said urine sample;

(iv) extracting RNA from the harvested cells;

(v) generating cDNA from said RNA by reverse transcription;

(vi) determining the expression level of at least hepsin and at least one reference gene by using gene specific primers and/or probes;

(vii) normalizing the expression level of at least hepsin with the determined expression level of said at least one reference gene; and (viii) attributing the presence or level of transcripts of hepsin and/or the expression level of hepsin to the presence of prostate cancer in said subject and/or an increased risk of said subject acquiring prostate cancer.

5. The method according to claim 4, wherein in addition to hepsin the expression of PCA3, EZH2 and prostein is analyzed.

* * * * *